United States Patent
Ishiyama

(10) Patent No.: US 10,660,189 B2
(45) Date of Patent: May 19, 2020

(54) X-RAY DIAGNOSIS SYSTEM AND ANODE-ROTATING COIL DRIVER

(71) Applicant: Canon Medical Systems Corporation, Otawara-shi (JP)

(72) Inventor: Fumio Ishiyama, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 177 days.

(21) Appl. No.: 15/987,434

(22) Filed: May 23, 2018

(65) Prior Publication Data

US 2018/0343727 A1  Nov. 29, 2018

(30) Foreign Application Priority Data

May 23, 2017 (JP) .................................. 2017-102102

(51) Int. Cl.
| | |
|---|---|
| H05G 1/18 | (2006.01) |
| H05G 1/56 | (2006.01) |
| H01J 35/10 | (2006.01) |
| H05G 1/70 | (2006.01) |
| H05G 1/58 | (2006.01) |
| A61B 6/00 | (2006.01) |
| A61B 6/04 | (2006.01) |

(52) U.S. Cl.
CPC .............. *H05G 1/18* (2013.01); *H01J 35/10* (2013.01); *H05G 1/56* (2013.01); *H05G 1/58* (2013.01); *H05G 1/70* (2013.01); *A61B 6/0407* (2013.01); *A61B 6/40* (2013.01); *A61B 6/42* (2013.01)

(58) Field of Classification Search
CPC . A61B 6/0407; A61B 6/40; A61B 6/42; H01J 35/10; H05G 1/18; H05G 1/56; H05G 1/58; H05G 1/70
See application file for complete search history.

(56) References Cited

U.S. PATENT DOCUMENTS

| | | | | |
|---|---|---|---|---|
| 3,335,280 A | * | 8/1967 | Wright, Jr. ............... | H05G 1/66 378/93 |
| 3,917,949 A | * | 11/1975 | Winkler .................... | H05G 1/46 378/94 |
| 2006/0233306 A1 | * | 10/2006 | Kitami ..................... | H05G 1/66 378/131 |
| 2013/0243161 A1 | | 9/2013 | Hishikawa | |

FOREIGN PATENT DOCUMENTS

| | | |
|---|---|---|
| JP | 7-46872 | 2/1995 |
| JP | 2000-150193 | 5/2000 |
| JP | 2011-109732 | 6/2011 |
| JP | 2016-91892 | 5/2016 |
| WO | WO 2012/073983 A1 | 6/2012 |

* cited by examiner

*Primary Examiner* — Marcus H Taningco
(74) *Attorney, Agent, or Firm* — Oblon, McClelland, Maier & Neustadt, L.L.P.

(57) ABSTRACT

An X-ray diagnosis system comprises an inter-capacitor terminal, a first inter-switching-element terminal, a second inter-switching-element terminal, and a third inter-switching-element terminal, wherein the first inter-switching-element terminal, the second inter-switching-element terminal, and the third inter-switching-element terminal are configured to supply three-phase alternating current power, and the inter-capacitor terminal and two of the first inter-switching-element terminal, the second inter-switching-element terminal, and the third inter-switching-element terminal are configured to supply two-phase alternating current power.

20 Claims, 16 Drawing Sheets

X-RAY DIAGNOSIS SYSTEM AND ANODE-ROTATING COIL DRIVER

CROSS-REFERENCE TO RELATED APPLICATIONS

This application is based upon and claims the benefit of priority from Japanese Patent Application No. 2017-102102, filed on May 23, 2017, the entire contents of all of which are incorporated herein by reference. The entire contents of the prior Japanese Patent Application No. 2018-098252, filed on May 22, 2018, are also incorporated herein by reference.

FIELD

Embodiments described herein relate generally to an X-ray diagnosis system and an anode-rotating coil driver.

BACKGROUND

In the field of X-ray image diagnosis, X-ray diagnosis systems including a plurality of image acquisition apparatuses have been used. Such an X-ray diagnosis system includes a first image acquisition apparatus and a second image acquisition apparatus, for example. The first image acquisition apparatus is, for example, an X-ray television. The X-ray television is used in gastrointestinal series, urography, myelography, or cholangiography, for example. To acquire an X-ray image at an appropriate timing by enabling a rotation of anode quickly, the first image acquisition apparatus is sometimes provided with a first X-ray tube having an anode driven by a three-phase alternating current. By contrast, the second image acquisition apparatus is a general X-ray image acquisition apparatus, for example. The second image acquisition apparatus is provided with a second X-ray tube having an anode driven by a two-phase alternating current because the second image acquisition apparatus has a longer time allowance for enabling rotation of anode, compared with that in the first image acquisition apparatus.

Therefore, an anode-rotating coil driver capable of driving both the first X-ray tube and the second X-ray tube has been developed. The first X-ray tube is connected to the anode-rotating coil driver, and the anode-rotating coil driver drives the anode of the first X-ray tube in rotation. The second X-ray tube is also connected to the anode-rotating coil driver, and the anode-rotating coil driver drives the anode of the second X-ray tube in rotation. To drive the first X-ray tube, for example, the anode-rotating coil driver controls a three-phase inverter in such a manner that a three-phase alternating current with a phase difference of 120 degrees is supplied. To drive the second X-ray tube, the anode-rotating coil driver controls the three-phase inverter in such a manner that a two-phase alternating current with a phase difference of 90 degrees is supplied. Such an anode-rotating coil driver, however, may cause an arm short circuit when supplied is a two-phase alternating current.

To prevent two coils provided to the second X-ray tube from being applied with a voltage simultaneously, there has been an anode-rotating coil driver that brings the width of a voltage pulse applied to the coils to one fourth or less of the cycle of the alternating current voltage to be output. However, such an anode-rotating coil driver sometimes requires a long time for enabling rotation of anode, because the effective voltage of the alternating current applied to the coils is low.

There is another anode-rotating coil driver that is provided with two inverters, and an isolation transformer inserted between the first X-ray tube or the second X-ray tube and each of the inverters. Any arm short circuit does not occur in this anode-rotating coil driver. However, because this anode-rotating coil driver is provided with the isolation transformer, the weight and the size of the anode-rotating coil driver are increased disadvantageously.

DETAILED DESCRIPTION

An X-ray diagnosis system comprises an inter-capacitor terminal, a first inter-switching-element terminal, a second inter-switching-element terminal, and a third inter-switching-element terminal. The inter-capacitor terminal is provided between two capacitors that are serially connected to each other. The first inter-switching-element terminal is provided between two first switching elements that are serially connected to each other. The second inter-switching-element terminal is provided between two second switching elements that are serially connected to each other. The third inter-switching-element terminal is provided between two third switching elements that are serially connected to each other. The first inter-switching-element terminal, the second inter-switching-element terminal, and the third inter-switching-element terminal are configured to supply three-phase alternating current power, and the inter-capacitor terminal and two of the first inter-switching-element terminal, the second inter-switching-element terminal, and the third inter-switching-element terminal are configured to supply two-phase alternating current power.

The X-ray diagnosis system and an anode-rotating coil driver according to some embodiments will now be explained with reference to some drawings. In the embodiments described below, redundant explanations will be omitted as appropriate.

Figure 1:
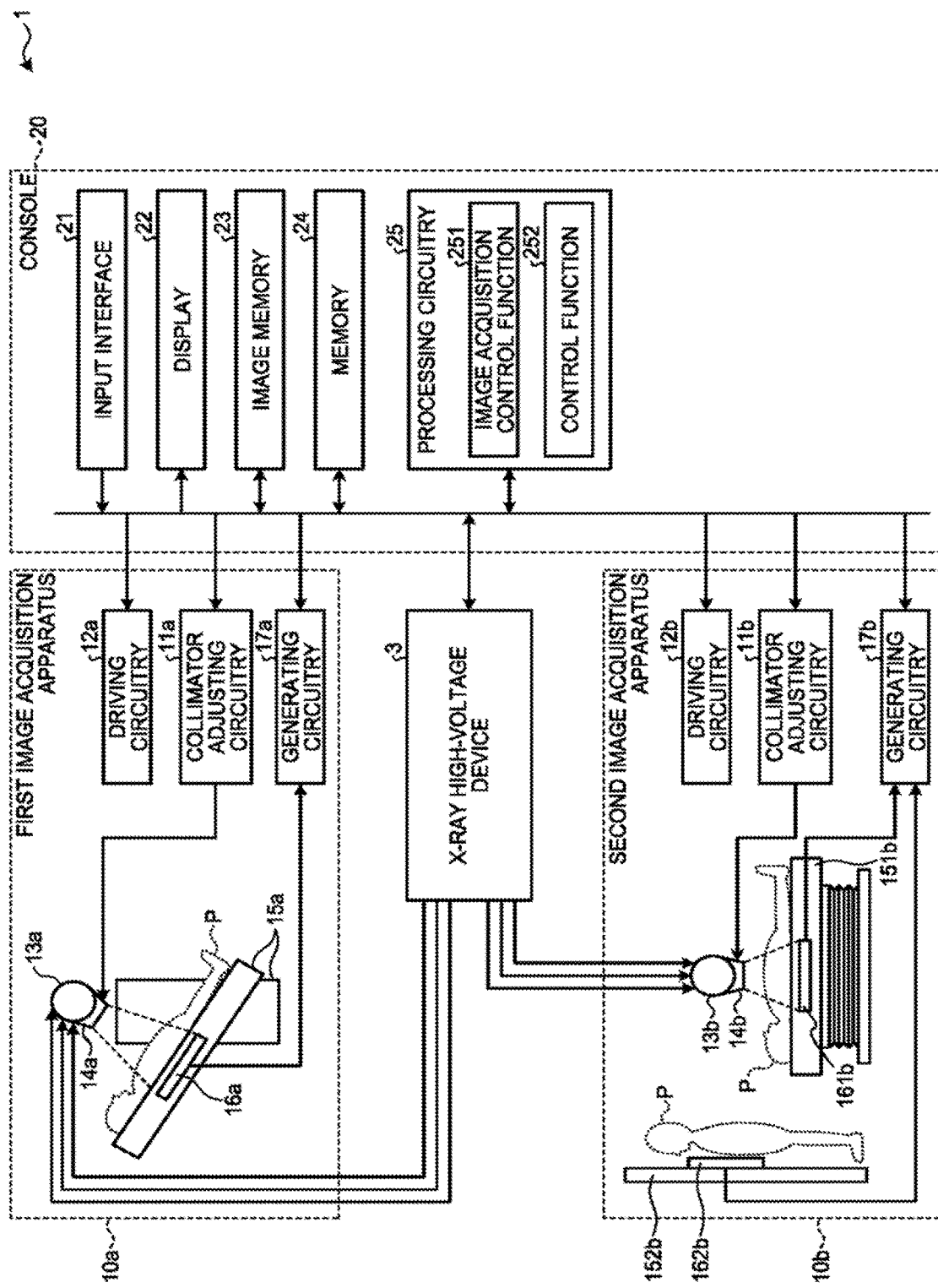
FIG. 1 is a block diagram illustrating an exemplary configuration of an X-ray diagnosis system according to a first embodiment.

To begin with, a configuration of an X-ray diagnosis system 1 according to a first embodiment will now be explained with reference to FIG. 1. FIG. 1 is a block diagram illustrating an exemplary configuration of the X-ray diagnosis system according to the first embodiment. The X-ray diagnosis system 1 includes, as illustrated in FIG. 1, a first image acquisition apparatus 10a, a second image acquisition apparatus 10b, a console 20, and an X-ray high-voltage device 3. The first image acquisition apparatus 10a is an X-ray television. The X-ray television is used in gastrointestinal series, urography, myelography, or cholangiography, for example. The first image acquisition apparatus 10a is also referred to as an R/F system. The second image acquisition apparatus 10b is a general X-ray image acquisition apparatus. The second image acquisition apparatus 10b is also referred to as an R system. The configuration of the X-ray diagnosis system 1 is, however, not limited to the configuration explained below.

The first image acquisition apparatus 10a includes collimator adjusting circuitry 11a, driving circuitry 12a, a first X-ray tube 13a, a collimator 14a, a couch 15a, a detector 16a, and generating circuitry 17a.

The collimator adjusting circuitry 11a adjusts the area irradiated with X-rays generated by the first X-ray tube 13a, by controlling the collimator 14a. Specifically, the collimator adjusting circuitry 11a adjusts the area irradiated with the X-rays by sliding the diaphragm blades provided to the collimator 14a. The collimator adjusting circuitry 11a implements this function by reading a computer program stored in a memory 24, which will be described later, and by executing the computer program.

The driving circuitry 12a drives the first X-ray tube 13a and the couch 15a. Specifically, the driving circuitry 12a adjusts the orientation and the position of the first X-ray tube 13a. The driving circuitry 12a adjusts the height, the position, and the inclination of the couchtop of the couch 15a. The driving circuitry 12a implements this function by reading a computer program stored in the memory 24, which will be described later, and executing the computer program.

The first X-ray tube 13a includes a cathode and an anode. The cathode emits electrons. The cathode is a filament made of tungsten, for example. The filament emits thermal electrons. Thermal electrons are electrons that become excited by heat generated by a current flowing through the filament, and jump out of the filament. The electrons emitted from the cathode are accelerated by a voltage applied between the anode and the cathode, and collide with the anode. The anode having received the electrons emitted from the cathode generates X-rays.

The first X-ray tube 13a is an X-ray tube that is driven by three-phase alternating current power, and includes three pairs of coils. Each pair of these coils is made by winding a lead wire into an annular shape. Each pair of coils is positioned in a manner facing the others with the anode interposed therebetween. The axes of these pairs of coils intersect with one another at one point on the rotational axis of the anode, and on a plane perpendicular to the rotational axis of the anode. The axis of each pair of coils forms an angle of 60 degrees with respect to the axes of the other pairs of coils. These coils require a voltage supply with a peak voltage of 280 V and an effective voltage of 200 V. These coils in the first X-ray tube 13a are driven by a voltage at an effective voltage of 200 V.

The collimator 14a adjusts the area irradiated with the X-rays generated by the first X-ray tube 13a. The collimator 14a includes four slidable X-ray diaphragm blades, for example. The collimator 14a adjusts the area irradiated with the X-rays generated by the first X-ray tube 13a by sliding these X-ray diaphragm blades.

The couch 15a has a couchtop on which a subject P is laid. The height, the position, and the inclination of the couchtop are adjusted by the driving circuitry 12a. The detector 16a is provided internal of the couchtop.

The detector 16a detects the X-rays emitted from the first X-ray tube 13a. The detector 16a is a flat panel detector (FPD), for example. The detector 16a includes detection elements that are arranged in a matrix. The detection elements convert the X-rays emitted from the first X-ray tube 13a into electric signals, and accumulate the electric signals. The accumulated electric signals are transmitted to the generating circuitry 17a.

The generating circuitry 17a generates an X-ray image based on the electric signals output from the detection elements. The generating circuitry 17a implements this function by reading a computer program stored in the memory 24, which will be described later, and executing the computer program. The generating circuitry 17a is implemented as a processor, for example.

The second image acquisition apparatus 10b includes collimator adjusting circuitry 11b, driving circuitry 12b, a second X-ray tube 13b, a collimator 14b, a couch 151b, a support member 152b, a detector 161b, a detector 162b, and generating circuitry 17b.

The collimator adjusting circuitry 11b, the collimator 14b, the detector 161b, the detector 162b, and the generating circuitry 17b are the same as the collimator adjusting circuitry 11a, the collimator 14a, the detector 16a, and the generating circuitry 17a that are included in the first image acquisition apparatus 10a.

The driving circuitry 12b drives the second X-ray tube 13b, the couch 151b, and the support member 152b. Specifically, the driving circuitry 12b adjusts the orientation and the position of the second X-ray tube 13b. The driving circuitry 12b adjusts the height and the position of the couchtop of the couch 151b. The driving circuitry 12b adjusts the height and the position of the detector 162b that is supported by the support member 152b.

The second X-ray tube 13b is an X-ray tube that is driven by two-phase alternating current power, and includes a common terminal and two pairs of coils. Each pair of these coils is made by winding a lead wire into an annular shape. Each of these pairs of coils is positioned in a manner facing the other with the anode interposed therebetween. The axis of each pair of coils intersects perpendicularly with the axis of the other pair of coils. These coils require a voltage supply with a peak voltage of 280 V and an effective voltage of 200 V. The coils in the second X-ray tube 13b are driven by a voltage with an effective voltage of 200 V, in the same manner as the coils in the first X-ray tube 13a.

The couch 151b has a couchtop on which the subject P is laid. The height and the position of the couchtop are adjusted by the driving circuitry 12b. The detector 161b is provided internal of the couchtop. The support member 152b supports the detector 162b.

The console 20 includes an input interface 21, a display 22, an image memory 23, the memory 24, and processing circuitry 25.

The input interface 21 is used by a user who is to enter an instruction or a setting. The input interface 21 is included in a mouse or a keyboard, for example. The input interface 21 transfers the instruction or the setting entered by the user to the processing circuitry 25. The input interface 21 is implemented as a processor, for example.

The display 22 is a monitor referred by a user. The display 22 is a liquid crystal display, for example. The display 22 receives an instruction for displaying an X-ray image or a graphical user interface (GUI) that is used when a user enters an instruction and a setting, for example, from the processing circuitry 25, and displays the X-ray image or the GUI.

The image memory 23 stores therein an X-ray image generated by the generating circuitry 17a, and an X-ray image generated by the generating circuitry 17b. The memory 24 stores therein computer programs for enabling the collimator adjusting circuitry 11a, the collimator adjusting circuitry 11b, the driving circuitry 12a, the driving circuitry 12b, the generating circuitry 17a, and the generating circuitry 17b to implement their functions. The memory 24 stores therein a computer program for enabling the processing circuitry 25 to implement each of the functions to be described later. The memory 24 stores therein a computer program for enabling control circuitry 9, which will be described later, to implement its function. The image memory 23 and the memory 24 are provided with storage media from which a computer can read information stored therein. One example of the storage media is a hard disk.

The processing circuitry 25 includes an image acquisition control function 251 and a control function 252. The processing circuitry 25 is implemented as a processor, for example.

The image acquisition control function 251 includes a function for acquiring an X-ray image, by controlling the collimator adjusting circuitry 11a, the driving circuitry 12a, the generating circuitry 17a, and the X-ray high-voltage device 3, which will be described later. The image acquisition control function 251 also includes a function for acquiring an X-ray image by controlling the collimator adjusting circuitry 11b, the driving circuitry 12b, the generating circuitry 17b, and the X-ray high-voltage device 3, which will be described later. The image acquisition control function 251 controls the first image acquisition apparatus 10a in the following manner, for example.

To begin with, the image acquisition control function 251 moves the first X-ray tube 13a, the collimator 14a, the couch 15a, and the detector 16a to positions that are suitable for acquiring an image, by controlling the driving circuitry 12a. The image acquisition control function 251 then irradiates the subject P with the X-rays, by controlling the collimator adjusting circuitry 11a and the X-ray high-voltage device 3. The image acquisition control function 251 then generates an X-ray image by controlling the generating circuitry 17a. To acquire a video, the image acquisition control function 251 performs this process to each frame of a video, by controlling the generating circuitry 17a. The image acquisition control function 251 also controls the second image acquisition apparatus 10b in the manner described above.

The control function 252 includes a function for causing the components included in the first image acquisition apparatus 10a, the second image acquisition apparatus 10b, the console 20, and the X-ray high-voltage device 3 to operate at appropriate timing, in a manner suitable for the purpose, and also includes other functions.

Figure 2:
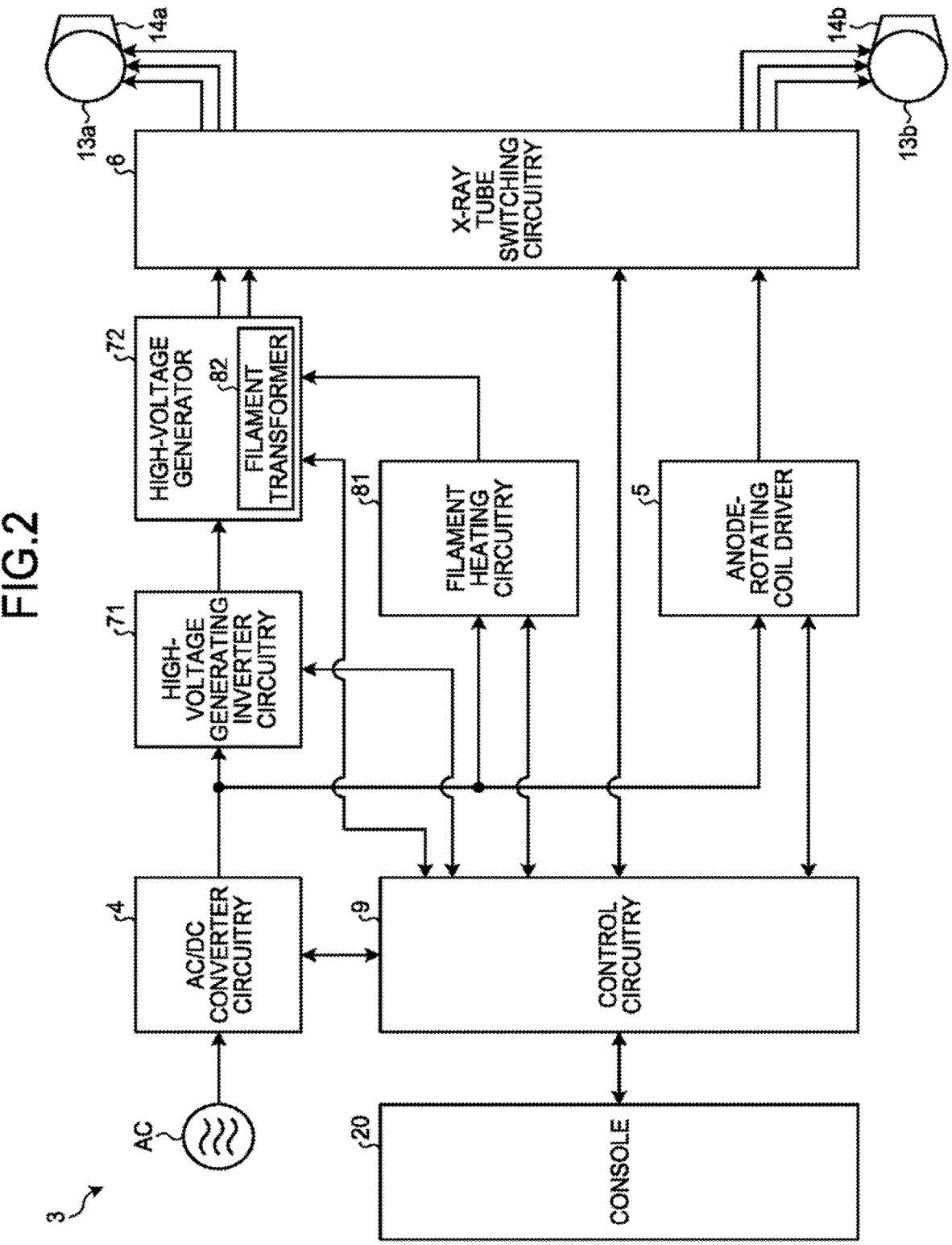
FIG. 2 is a block diagram illustrating an exemplary configuration of an X-ray high-voltage device according to the first embodiment.

The X-ray high-voltage device 3 illustrated in FIG. 1 will now be generally explained with reference to FIG. 2. FIG. 2 is a block diagram illustrating an exemplary configuration of the X-ray high-voltage device according to the first embodiment. The X-ray high-voltage device 3 includes, as illustrated in FIG. 2, AC/DC converter circuitry 4, an anode-rotating coil driver 5, X-ray tube switching circuitry 6, high-voltage generating inverter circuitry 71, a high-voltage generator 72, filament heating circuitry 81, a filament transformer 82, and the control circuitry 9.

The AC/DC converter circuitry 4 generates a direct-current voltage from an alternating current supplied from a three-phase alternating current power source AC that is a power source. The AC/DC converter circuitry 4 receives the supply of the three-phase alternating current from the three-phase alternating current power source AC. The three-phase alternating current power source AC supplies a three-phase alternating current at an effective voltage of 400 V, or a three-phase alternating current at an effective voltage of 200 V, for example. The AC/DC converter circuitry 4 generates a direct-current voltage by full-wave rectifying the three-phase alternating current. The AC/DC converter circuitry 4 supplies the direct-current voltage to the anode-rotating coil driver 5, the high-voltage generating inverter circuitry 71, and the filament heating circuitry 81.

The anode-rotating coil driver 5 converts the direct-current voltage supplied from the AC/DC converter circuitry 4 into a three-phase alternating current. The anode-rotating coil driver 5 supplies the three-phase alternating current to the three pairs of coils included in the first X-ray tube 13a, and drives the anode of the first X-ray tube 13a in rotation. The anode-rotating coil driver 5 also converts the direct-current voltage supplied from the AC/DC converter circuitry 4 into a two-phase alternating current. The anode-rotating coil driver 5 then supplies the two-phase alternating current to the two pairs of coils included in the second X-ray tube 13b, and drives the anode of the second X-ray tube 13b in rotation.

The high-voltage generating inverter circuitry 71 converts the direct-current voltage generated by the AC/DC converter circuitry 4 into an alternating current voltage, and supplies the alternating current voltage to the high-voltage generator 72. The high-voltage generator 72 converts an alternating current voltage into a direct-current voltage while stepping up the voltage, and supplies the resultant voltage to the first X-ray tube 13a or the second X-ray tube 13b as a tube voltage.

The filament heating circuitry 81 converts the direct-current voltage generated by the AC/DC converter circuitry 4 into an alternating current voltage, and supplies the alternating current voltage to the filament transformer 82. The filament transformer 82 controls the current flowing through the filament in the first X-ray tube 13a or the second X-ray tube 13b. The filament transformer 82 insulates the filament included in the first X-ray tube 13a or the second X-ray tube 13b from the filament heating circuitry 81. The filament transformer 82 is included in the high-voltage generator 72, as illustrated in FIG. 2.

The X-ray tube switching circuitry 6 switches to a configuration in which the anode-rotating coil driver 5 is connected to the first X-ray tube 13a, and to another configuration in which the anode-rotating coil driver 5 is connected to the second X-ray tube 13b. The X-ray tube switching circuitry 6 also switches to a configuration in which the high-voltage generator 72 is connected to the first X-ray tube 13a, and to a configuration in which the high-voltage generator 72 is connected to the second X-ray tube 13b.

The control circuitry 9 controls the AC/DC converter circuitry 4, the anode-rotating coil driver 5, the X-ray tube switching circuitry 6, the high-voltage generating inverter circuitry 71, the high-voltage generator 72, the filament heating circuitry 81, and the filament transformer 82, in a manner suitable for the purpose. The control circuitry 9 implements this function by reading a computer program stored in the memory 24, and executing the computer program. The control circuitry 9 is implemented as a processor, for example.

Figure 3:
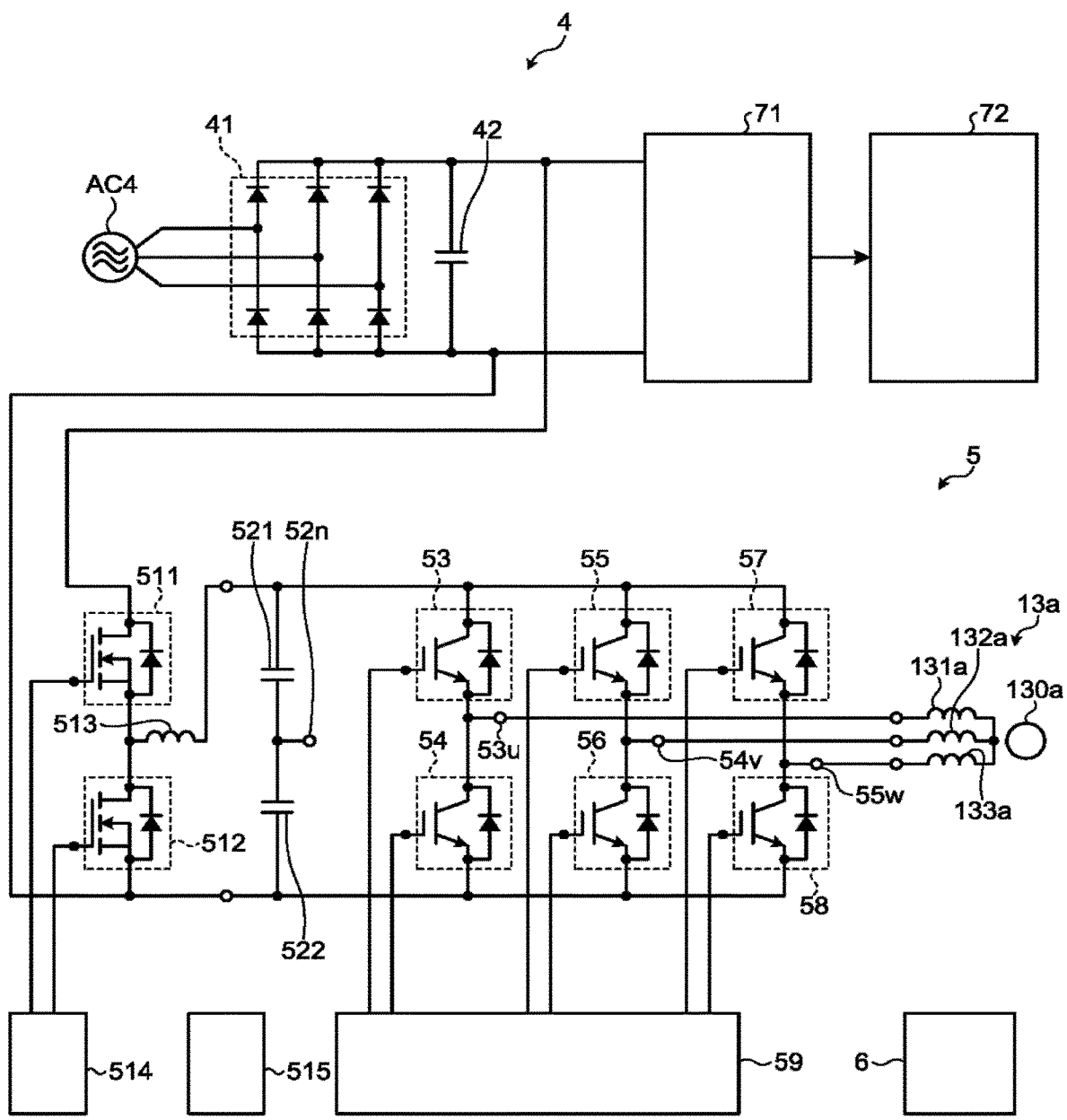
FIG. 3 is a schematic illustrating an exemplary circuit configuration of an anode-rotating coil driver according to the first embodiment at the time when the anode-rotating coil driver supplies a three-phase alternating current to a first X-ray tube.

The AC/DC converter circuitry 4, the anode-rotating coil driver 5, the X-ray tube switching circuitry 6, the high-voltage generating inverter circuitry 71, and the high-voltage generator 72 will now be explained in detail with reference to FIG. 3. FIG. 3 is a schematic illustrating an exemplary circuit configuration of the anode-rotating coil driver at the time when the anode-rotating coil driver according to the first embodiment supplies a three-phase alternating current to the first X-ray tube.

The first X-ray tube 13a is an X-ray tube in which an anode 130a is driven by a three-phase alternating current, and includes three pairs of coils (a coil 131a, a coil 132a, and a coil 133a), as illustrated in FIG. 3. In the example illustrated in FIG. 3, one ends of the coil 131a, the coil 132a, and the coil 133a are connected in a star connection. These coils are supplied with the three-phase alternating current from the anode-rotating coil driver 5, and generate a rotating magnetic field. The anode 130a is caused to rotate by the rotating magnetic field.

The AC/DC converter circuitry 4 includes, as illustrated in FIG. 3, a three-phase rectifier diode bridge 41 and a smoothing capacitor 42. The three-phase rectifier diode bridge 41 is connected to a three-phase alternating current power source AC4. The three-phase alternating current power source AC4 illustrated in FIG. 3 is a power source that generates a three-phase alternating current at an effective voltage of 400 V. The three-phase alternating current power source AC4 has three output terminals, and these three output terminals are connected to the three-phase rectifier diode bridge 41.

The two terminals of the smoothing capacitor 42 are connected to the high-voltage generating inverter circuitry 71. The high-voltage generating inverter circuitry 71 is connected to the high-voltage generator 72. In FIG. 3, the AC/DC converter circuitry 4 being supplied with the three-phase alternating current at an effective voltage of 400 V from the AC4 generates a direct-current voltage at 560 V, and supplies the generated 560-V direct-current voltage to the high-voltage generating inverter circuitry 71, and to the anode-rotating coil driver 5.

The anode-rotating coil driver 5 includes an n-type metal oxide semiconductor field effect transistor (MOSFET) 511, an n-type MOSFET 512, a step-up/step-down coil 513, step-up/step-down switching element driving circuitry 514, and step-up/step-down switching circuitry 515. The n-type MOSFET 511, the n-type MOSFET 512, the step-up/step-down coil 513, and the step-up/step-down switching element driving circuitry 514 make up a step-up/step-down converter. The n-type MOSFET 511 is also referred to as a first step-up/step-down switching element, and the n-type MOSFET 512 is also referred to as a second step-up/step-down switching element.

The n-type MOSFET 511 and the n-type MOSFET 512 are serially connected to each other, with one end of the step-up/step-down coil 513 interposed therebetween. In other words, the source of the n-type MOSFET 511, the drain of the n-type MOSFET 512, and one end of the step-up/step-down coil 513 are connected to one another. The drain of the n-type MOSFET 511 is connected to the high-voltage-side terminal of the smoothing capacitor 42. The source of the n-type MOSFET 512 is connected to the low-voltage-side terminal of the smoothing capacitor 42 and to the low-voltage-side terminal of a capacitor 522, which will be described later. The other end of the step-up/step-down coil 513 is connected to the high-voltage-side terminal of a capacitor 521, which will be described later. The step-up/step-down switching element driving circuitry 514 is connected to the gate of the n-type MOSFET 511 and the gate of the n-type MOSFET 512. In other words, the step-up/step-down converter is inserted between the AC/DC converter circuitry 4, and the capacitor 521 and the capacitor 522, both of which will be explained below. A configuration and the like of the step-up/step-down converter illustrated in FIG. 3 will be described later in detail.

The anode-rotating coil driver 5 includes two capacitors (the capacitor 521 and the capacitor 522) that are serially connected to each other with an inter-capacitor terminal 52n interposed therebetween. The anode-rotating coil driver 5 also includes two first switching elements (a first switching element 53 and a first switching element 54) that are serially connected to each other, with a first inter-switching-element terminal 53u interposed therebetween. The anode-rotating coil driver 5 also includes two second switching elements (a second switching element 55 and a second switching element 56) that are serially connected to each other with a second inter-switching-element terminal 54v interposed therebetween. The anode-rotating coil driver 5 also includes two third switching elements (a third switching element 57 and a third switching element 58) that are serially connected to each other with a third inter-switching-element terminal 55w interposed therebetween. The two capacitors, the two first switching elements, the two second switching elements, and the two third switching elements are connected to the AC4 that is a power source via the AC/DC converter circuitry 4 and the step-up/step-down converter.

Illustrated in FIG. 3 is an example in which each of the first switching elements 53 and 54, the second switching elements 55 and 56, and the third switching elements 57 and 58 makes up an anti-parallel circuit of an insulated gate bipolar transistor (IGBT) and a diode, but a bipolar transistor, a power MOSFET, or a junction FET may also be used instead of the IGBT.

The low-voltage-side terminal of the capacitor 521 and the high-voltage-side terminal of the capacitor 522 are connected to the inter-capacitor terminal 52n. The capacitance of the capacitor 521 is equal to that of the capacitor 522. The high-voltage-side terminal of the capacitor 521 is connected to the other end of the step-up/step-down coil 513. The low-voltage-side terminal of the capacitor 522 is connected to the source of the n-type MOSFET 512 and to the low-voltage-side terminal of the smoothing capacitor 42.

Switching element driving circuitry 59 is connected to the gates of the first switching elements 53 and 54, to the gates of the second switching elements 55 and 56, to the gates of the third switching elements 57 and 58.

The X-ray tube switching circuitry 6 switches to supply power to the first X-ray tube 13a that is driven by the three-phase alternating current power, and to supply power to the second X-ray tube 13b that is driven by the two-phase alternating current power, based on the outputs at the inter-capacitor terminal 52n, the first inter-switching-element terminal 53u, the second inter-switching-element terminal 54v, and the third inter-switching-element terminal 55w.

To cause the first X-ray tube 13a to emit X-rays, the X-ray tube switching circuitry 6 supplies power to the first X-ray tube 13a via the first inter-switching-element terminal 53u, the second inter-switching-element terminal 54v, and the third inter-switching-element terminal 55w. In other words, as illustrated in FIG. 3, to cause the first X-ray tube 13a to emit X-rays, the X-ray tube switching circuitry 6 connects the first inter-switching-element terminal 53u to the coil 131a, connects the second inter-switching-element terminal 54v to the coil 132a, and connects the third inter-switching-element terminal 55w to the coil 133a. The X-ray tube switching circuitry 6 connects the inter-capacitor terminal 52n to none of the coils 131a, 132a, and 133a, as illustrated in FIG. 3.

Figure 4:
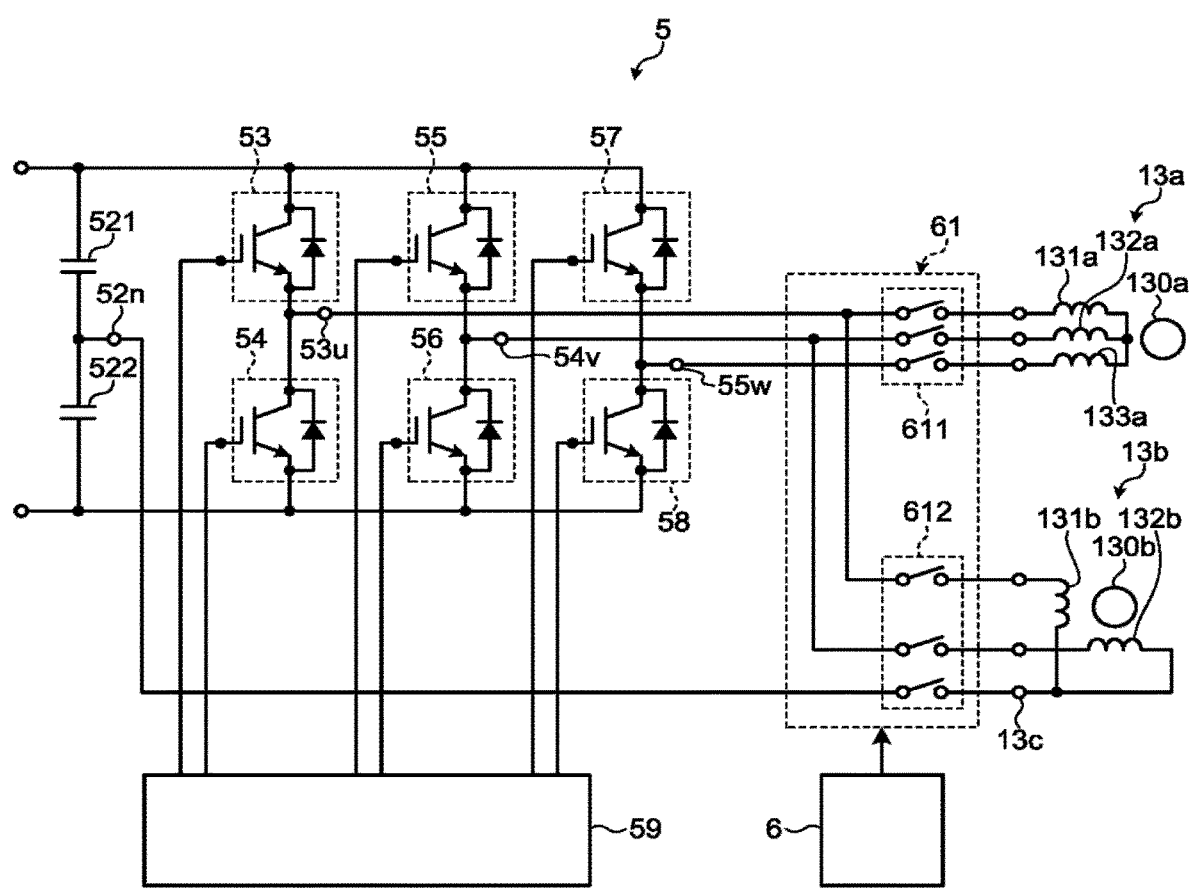
FIG. 4 is a schematic for explaining X-ray tube switching circuitry.

FIG. 4 is a schematic for explaining the X-ray tube switching circuitry. The X-ray tube switching circuitry 6 controls to switch a switch group 61 illustrated in FIG. 4 to ON/OFF. To cause the first X-ray tube 13a to emit X-rays, the X-ray tube switching circuitry 6 switches a first switch group 611 illustrated in FIG. 4 to ON, and switches a second switch group 612 illustrated in FIG. 4 to OFF. The first switch group 611 includes a switch provided to a lead wire connecting the first inter-switching-element terminal 53u and the coil 131a, a switch provided to a lead wire connecting the second inter-switching-element terminal 54v and the coil 132a, and a switch provided to a lead wire connecting the third inter-switching-element terminal 55w and the coil 133a.

By setting "the first switch group 611: ON, the second switch group 612: OFF", the anode-rotating coil driver 5 comes to have a configuration with a three-phase full-bridge inverter circuit that uses three sets of "two switching elements", as illustrated in FIG. 3, as a starter of the anode 130a.

To cause the second X-ray tube 13b to emit X-rays, the X-ray tube switching circuitry 6 switches the first switch group 611 to OFF, and switches the second switch group 612 to ON. The example in which the second X-ray tube 13b is caused to emit X-rays will be described later.

The step-up/step-down converter including the n-type MOSFET 511, the n-type MOSFET 512, the step-up/step-down coil 513, and the step-up/step-down switching element driving circuitry 514, and the step-up/step-down switching circuitry 515 will now be explained. The three-phase alternating current power source AC4 supplies a three-phase alternating current at an effective voltage of 400 V to the three-phase rectifier diode bridge 41. The smoothing capacitor 42 outputs a 560-V direct-current voltage to the anode-rotating coil driver 5. The coil 131a, the coil 132a, and the coil 133a in the first X-ray tube 13a are, however, driven by a 280-V alternating current voltage with an effective voltage of 200 V. Therefore, it is necessary, in the three-phase full-bridge inverter circuit, to apply a 280-V direct-current voltage between the high-potential side of the capacitor 521 and the low-potential side of the capacitor 522. The input voltage of the three-phase full-bridge inverter circuit serves as a voltage for driving the first X-ray tube 13a and the second X-ray tube 13b. Therefore, to drive the first X-ray tube 13a using the three-phase alternating current at an effective voltage of 400 V as an input, the 560-V direct-current voltage needs to be stepped down to the 280-V direct-current voltage using the step-up/step-down converter.

The step-up/step-down switching circuitry 515 switches to a configuration for stepping down the direct-current voltage generated by the AC/DC converter circuitry 4, to a configuration for stepping up the direct-current voltage generated by the AC/DC converter circuitry 4, and to a configuration for not stepping down or stepping up the direct-current voltage.

To step down the voltage, as illustrated in FIG. 3, the step-up/step-down switching circuitry 515 connects the low-voltage-side terminal of the step-up/step-down converter (the source of the n-type MOSFET 512) to the low-voltage-side terminal of the AC/DC converter circuitry 4 (the low-voltage-side terminal of the smoothing capacitor 42) and to the low-voltage-side terminal of the two capacitors 521 and 522 (low-voltage-side terminal of the capacitor 522). To step down the voltage, as illustrated in FIG. 3, the step-up/step-down switching circuitry 515 also connects the high-voltage-side terminal of the step-up/step-down converter (the drain of the n-type MOSFET 511) to the high-voltage-side terminal of the AC/DC converter circuitry 4 (high-voltage-side terminal of the smoothing capacitor 42). To step down the voltage, as illustrated in FIG. 3, the step-up/step-down switching circuitry 515 also connects the other end of the step-up/step-down coil 513 to the high-voltage-side terminal of the two capacitors 521 and 522 (the high-voltage-side terminal of the capacitor 521).

This connection enables the step-up/step-down converter to function as a step-down converter, and the voltage resultant of stepping down the 560-V direct-current voltage generated by the AC/DC converter circuitry 4 is applied to the capacitor 521 and the capacitor 522. The step-up/step-down converter operates in the manner described below, for example.

The step-up/step-down switching element driving circuitry 514 supplies a voltage pulse (ON signal) to the gate of the n-type MOSFET 511 and the gate of the n-type MOSFET 512. In other words, the step-up/step-down switching element driving circuitry 514 applies a voltage to the gates of the n-type MOSFET 511 and the n-type MOSFET 512, using the potential at the source of the n-type MOSFET 511 and the source of the n-type MOSFET 512 as a reference. By supplying the voltage pulse, the step-up/step-down switching element driving circuitry 514 causes the n-type MOSFET 511 and the n-type MOSFET 512 to be switched to ON alternatingly at a constant cycle. The n-type MOSFET 511 and the n-type MOSFET 512 are switched to ON alternatingly at a duty ratio expressed by Equation below, where Ton denotes the time for which the n-type MOSFET 511 is ON, and Toff denotes the time for which the n-type MOSFET 511 is OFF.

$$D = \frac{Ton}{Ton + Toff} \approx 0.5$$

In other words, the n-type MOSFET 511 and the n-type MOSFET 512 are switched to ON alternatingly at a duty ratio of approximately 0.5. In this manner, the step-up/step-down converter steps down the 560-V direct-current voltage generated by the AC/DC converter circuitry 4 to 280 V. The relation between these voltages and the duty ratio is expressed by the following Equation, where Vin denotes the 560-V direct-current voltage generated by the AC/DC converter circuitry 4, and Vout denotes the 280-V direct-current voltage output from the step-up/step-down converter.

$$Vout = D \cdot Vin = 0.5 \times 560 = 280$$

Figure 5:
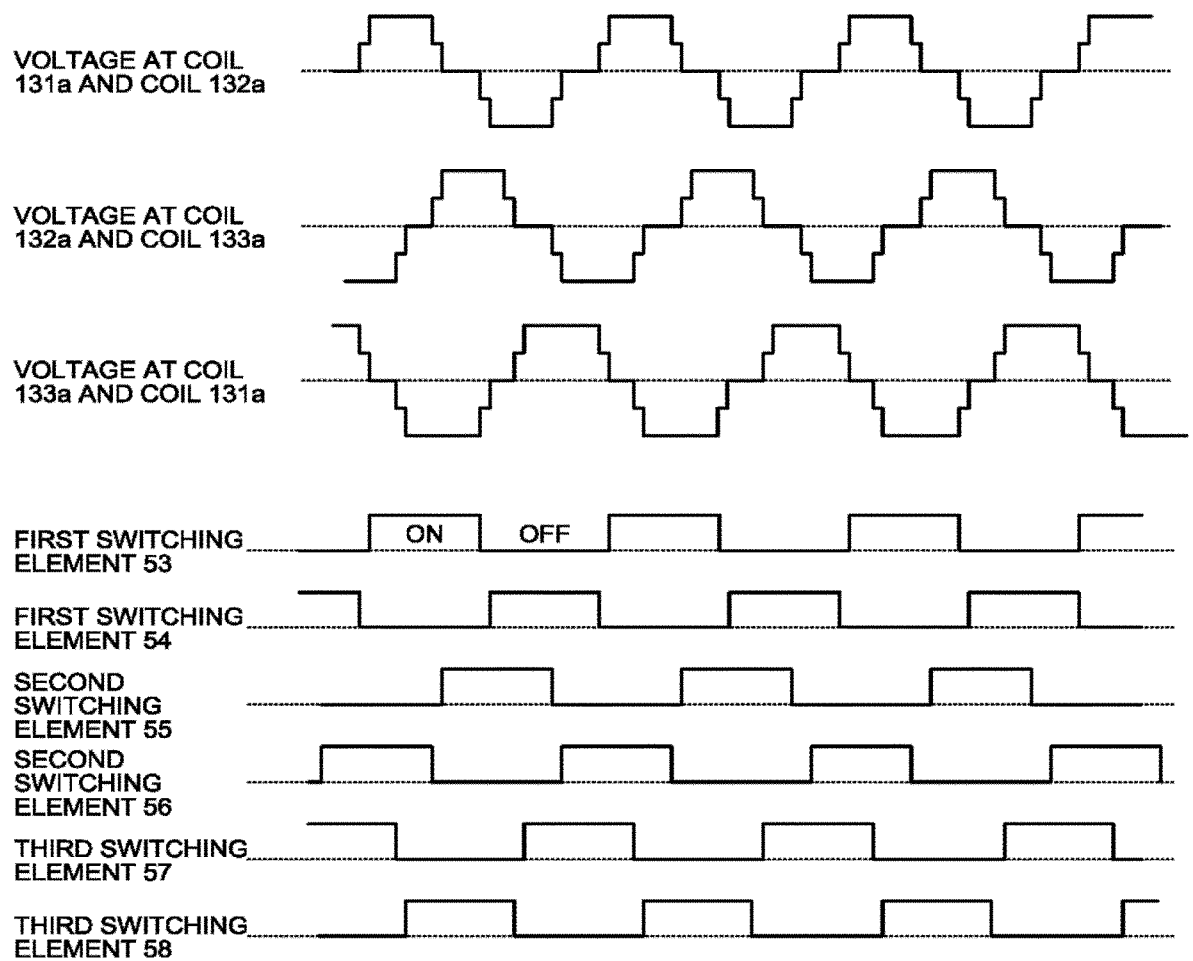
FIG. 5 is a timing chart illustrating a relation between voltages applied to the coils in the first X-ray tube and ON/OFF of switching elements in the first embodiment.

A method by which the anode-rotating coil driver 5 according to the first embodiment drives the first X-ray tube 13a will now be explained, with reference to FIG. 5. FIG. 5 is a timing chart illustrating a relation between the voltages applied to the coils in the first X-ray tube, and ON/OFF of the switching elements in the first embodiment.

The 280-V direct-current voltage output from the step-up/step-down converter is applied to the capacitor 521 and the capacitor 522. The switching element driving circuitry 59 supplies a voltage pulse to the first switching element 53, the first switching element 54, the second switching element 55, the second switching element 56, the third switching element 57, and the third switching element 58. The switching element driving circuitry 59 supplies the voltage pulse to the switching elements at the timing illustrated in FIG. 5, for example. In this manner, the switching element driving circuitry 59 controls the ON and OFF of the switching elements so that the three-phase alternating current is produced by the three-phase full-bridge inverter circuit.

When the first switching element 53 is ON, the first switching element 54 is OFF, and the second switching element 56 is ON, a +280-V voltage with reference to the second inter-switching-element terminal 54v is applied between the first inter-switching-element terminal 53u and the second inter-switching-element terminal 54v. In other words, in such a configuration, the coil 131a and the coil 132a are applied with a +280-V voltage with reference to the second inter-switching-element terminal 54v. The +280-V voltage is the 280-V voltage applied to the capacitor 521 and the capacitor 522.

When the first switching element 53 is OFF, the first switching element 54 is ON, and the second switching element 55 is ON, a −280-V voltage with reference to the second inter-switching-element terminal 54v is applied between the first inter-switching-element terminal 53u and the second inter-switching-element terminal 54v. In other words, in such a configuration, the coil 131a and the coil 132a are applied with a −280-V voltage with reference to the second inter-switching-element terminal 54v. The −280-V voltage is the 280-V voltage that is applied to the capacitor 521 and the capacitor 522.

In other words, the switching element driving circuitry 59 switches the first switching element 53 and the first switching element 54 to ON alternatingly at a constant cycle, and switches the second switching element 56 or the second switching element 55 to ON accordingly. In this manner, the switching element driving circuitry 59 supplies a rectangular-wave alternating current illustrated in FIG. 5 to the coil 131a and the coil 132a. The voltage applied to the coil 131a and the coil 132a is also referred to as a line voltage.

In the same manner, the switching element driving circuitry 59 switches the second switching element 55 and the second switching element 56 to ON alternatingly at a constant cycle, and switches the third switching element 58 or the third switching element 57 to ON accordingly. In this manner, the switching element driving circuitry 59 supplies the rectangular-wave alternating current illustrated in FIG. 5 to the coil 132a and the coil 133a. The switching element driving circuitry 59 also switches the third switching element 57 and the third switching element 58 to ON alternatingly at a constant cycle, and switches the first switching element 54 or the first switching element 53 to ON accordingly. In this manner, the switching element driving circuitry 59 supplies the rectangular-wave alternating current illustrated in FIG. 5 to the coil 133a and the coil 131a.

The rectangular wave alternating current supplied to the coil 131a and the coil 132a, the rectangular wave alternating current supplied to the coil 132a and the coil 133a, and the rectangular wave alternating current supplied to the coil 133a and the coil 131a all have the same cycle.

The switching element driving circuitry 59 adds a delay of ⅓ of the cycle of the rectangular wave alternating current to the timing at which the second switching element 55 and the second switching element 56 are switched to ON alternatingly, with respect to the timing at which the first switching element 53 and the first switching element 54 are switched to ON alternatingly. Therefore, the phase of the rectangular wave alternating current supplied to the coil 132a and the coil 133a is 120 degrees behind the phase of the rectangular wave alternating current supplied to the coil 131a and the coil 132a. Furthermore, the switching element driving circuitry 59 adds a delay of ⅔ of the cycle of the rectangular wave alternating current to the timing at which the third switching element 57 and the third switching element 58 are switched to ON alternatingly, with respect to the timing at which the first switching element 53 and the first switching element 54 are switched to ON alternatingly. Therefore, the phase of the rectangular wave alternating current supplied to the coil 133a and the coil 131a is 240 degrees behind the phase of the rectangular wave alternating current supplied to the coil 131a and the coil 132a.

During the period from when the first switching element 53 is switched to OFF to when the first switching element 54 is switched to ON and during the period from when the first switching element 54 is switched to OFF to when the first switching element 53 is switched to ON, the first switching elements 53 and 54 are both OFF. During the period from when the second switching element 55 is switched to OFF to when the second switching element 56 is switched to ON, and the period from when the second switching element 56 is switched to OFF to when the second switching element 55 is switched to ON, the second switching elements 55 and 56 are both OFF. During the period from when the third switching element 57 is switched to OFF to when the third switching element 58 is switched to ON, and during the period from when the third switching element 58 is switched to OFF to when the third switching element 57 is switched to ON, the third switching elements 57 and 58 are both OFF. These periods are dead time.

The voltage of the rectangular wave alternating current supplied to the coil 131a and the coil 132a remains at zero for some period and becomes reversed, as illustrated in FIG. 5. The length of this period is approximately ⅙ of the cycle of the rectangular wave alternating current. The voltage at the first inter-switching-element terminal 53u, the voltage at the second inter-switching-element terminal 54v, and the voltage at the third inter-switching-element terminal 55w are zero except for the IGBT dead time. Through the operation described above, the coil 131a, the coil 132a, and the coil 133a generate a rotating magnetic field. This rotating magnetic field causes the anode 130a to rotate.

Figure 6:
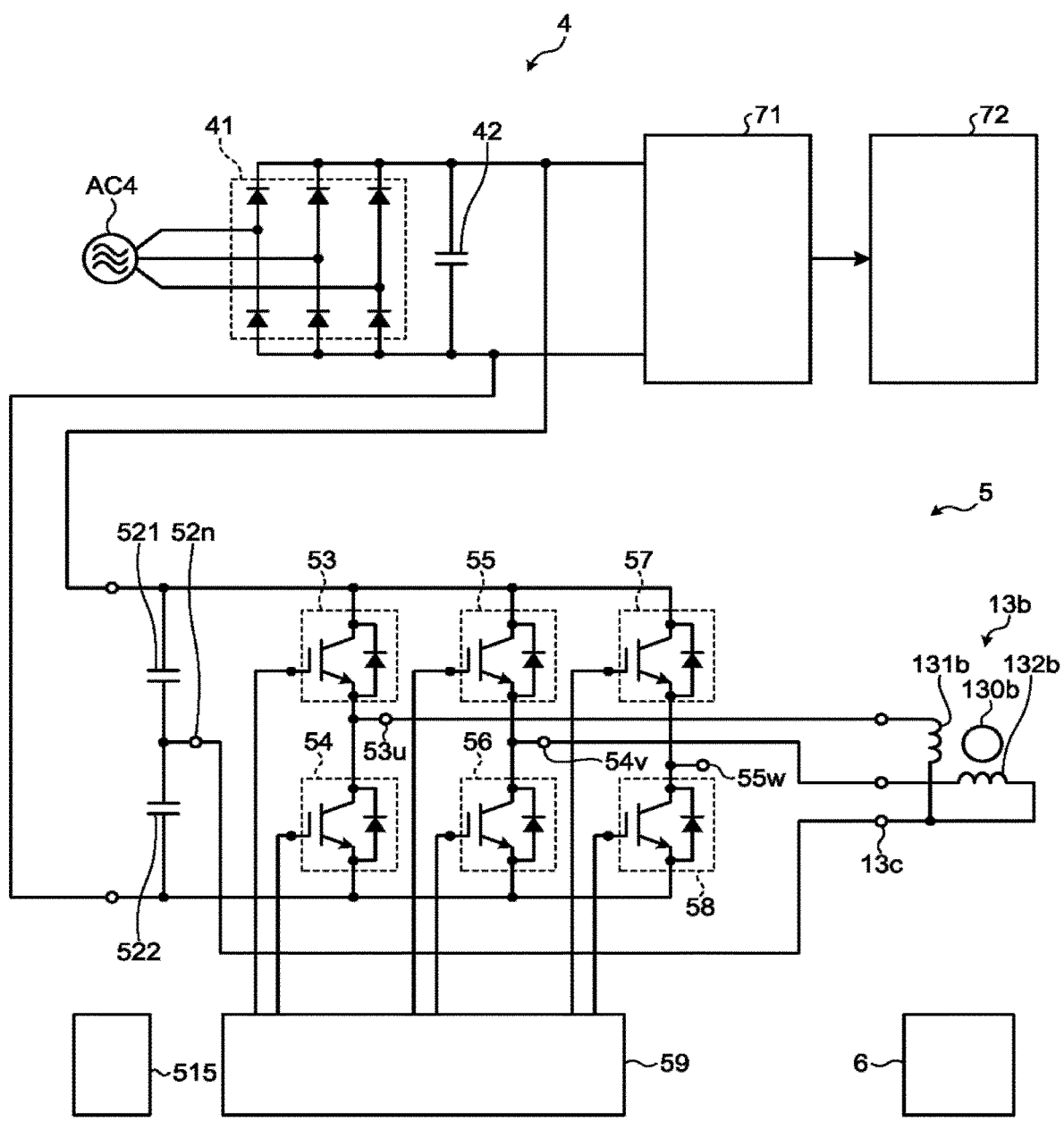
FIG. 6 is a schematic illustrating an exemplary circuit configuration of the anode-rotating coil driver according to the first embodiment at the time when the anode-rotating coil driver supplies a two-phase alternating current to a second X-ray tube.

An example in which the anode-rotating coil driver 5 drives the second X-ray tube 13b will now be explained with reference to FIG. 6. FIG. 6 is a schematic illustrating an exemplary circuit configuration of the anode-rotating coil driver at the time when the anode-rotating coil driver according to the first embodiment supplies a two-phase alternating current to the second X-ray tube. As to the matters that are redundant with those in the explanations of the AC/DC converter circuitry 4, the anode-rotating coil driver 5, the X-ray tube switching circuitry 6, the high-voltage generating inverter circuitry 71, and the high-voltage generator 72, explained with reference to FIG. 3, explanations of such matters will be omitted.

The second X-ray tube 13b is an X-ray tube in which an anode 130b is driven by a two-phase alternating current, and includes two pairs of coils (a coil 131b and a coil 132b) and a common terminal 13c, as illustrated in FIG. 6. One end of the coil 131b and one end of the coil 132b are connected to the common terminal 13c. These coils receive a supply of the two-phase alternating current from the anode-rotating coil driver 5, and generates a rotating magnetic field. This rotating magnetic field causes the anode 130b to rotate. One of the coil 131b and the coil 132b is referred to as a main coil, and the other coil is referred to as an auxiliary coil.

The AC/DC converter circuitry 4 illustrated in FIG. 6 has the three-phase rectifier diode bridge 41 and the smoothing capacitor 42, in the same manner as illustrated in FIG. 3, and the three-phase rectifier diode bridge 41 is connected to the three-phase alternating current power source AC4 that generates a three-phase alternating current at an effective voltage of 400 V. The AC/DC converter circuitry 4 generates 560-V direct-current voltage, and supplies the generated 560-V direct-current voltage to the high-voltage generating inverter circuitry 71, and to the anode-rotating coil driver 5.

The high-voltage-side terminal of the capacitor 521 is connected to the high-voltage-side terminal of the smoothing capacitor 42. The low-voltage-side terminal of the capacitor 522 is connected to the low-voltage-side terminal of the smoothing capacitor 42. In other words, because the step-up/step-down converter does not step up nor step down the direct-current voltage generated by the AC/DC converter circuitry 4, the step-up/step-down converter is not inserted between the AC/DC converter circuitry 4, and the capacitor 521 and the capacitor 522. The reason will be described later.

To cause the second X-ray tube 13b to emit X-rays, the X-ray tube switching circuitry 6 supplies power to the second X-ray tube 13b via the inter-capacitor terminal 52n, and two of the first inter-switching-element terminal 53u, the second inter-switching-element terminal 54v, and the third inter-switching-element terminal 55w. In other words, the X-ray tube switching circuitry 6 connects the inter-capacitor terminal 52n to the common terminal 13c, and connects two of the first inter-switching-element terminal 53u, the second inter-switching-element terminal 54v, and the third inter-switching-element terminal 55w to the coil 131b and the coil 132b, respectively, in the second X-ray tube 13b. The X-ray tube switching circuitry 6 connects these terminals as illustrated in FIG. 6, for example.

The inter-capacitor terminal 52n is connected to the common terminal 13c in the second X-ray tube 13b. The first inter-switching-element terminal 53u is connected to the coil 131b in the second X-ray tube 13b. The second inter-switching-element terminal 54v is connected to the coil 132b in the second X-ray tube 13b. The third inter-switching-element terminal 55w is connected to none of the coil 131b and the coil 132b in the second X-ray tube 13b. In such a configuration, the coil 131b is also referred to as a main coil, and the coil 132b is also referred to as the auxiliary coil.

The connection illustrated in FIG. 6 is achieved using the second switch group 612 illustrated in FIG. 4. The second switch group 612 illustrated in FIG. 4 includes a switch provided to a lead wire connecting the first inter-switching-element terminal 53u and the coil 131b, a switch provided to a lead wire connecting the second inter-switching-element terminal 54v and the coil 132b, and a switch provided to the lead wire connecting the inter-capacitor terminal 52n and the common terminal 13c.

By setting "the first switch group 611: OFF, the second switch group 612: ON", the anode-rotating coil driver 5 comes to have a configuration with a single-phase half bridge inverter circuit that uses a neutral point (the inter-capacitor terminal 52n) and two sets of "two switching elements", as illustrated in FIG. 6, as a starter of the anode 130b.

The smoothing capacitor 42 outputs 560-V direct-current voltage to the anode-rotating coil driver 5. The coil 131b and the coil 132b in the second X-ray tube 13b are driven by a 280-V alternating current voltage at an effective voltage of 200 V. Therefore, it is necessary, in the single-phase half bridge inverter circuit, to apply +280 V to the high-potential side of the capacitor 521, and to apply −280 V to the low-potential side of the capacitor 522, with reference to the neutral point. The input voltage to the single-phase half bridge inverter circuit is twice the driving voltage for the first X-ray tube 13a and the second X-ray tube 13b. Therefore, to drive the second X-ray tube 13b using the three-phase alternating current at an effective voltage of 400 V as an input, the 560-V direct-current voltage output from the smoothing capacitor 42 may be supplied to the starter without stepping up or down the voltage.

In such a case, the step-up/step-down switching circuitry 515 connects the high-voltage-side terminal of the AC/DC converter circuitry 4 (the high-voltage-side terminal of the smoothing capacitor 42) to the high-voltage-side terminal of the two capacitors 521 and 522 (high-voltage-side terminal of the capacitor 521), and connects the low-voltage-side terminal of the AC/DC converter circuitry 4 (the low-voltage-side terminal of the smoothing capacitor 42) to the low-voltage-side terminal of two capacitors 521 and 522 (the low-voltage-side terminal of the capacitor 522).

Figure 7:
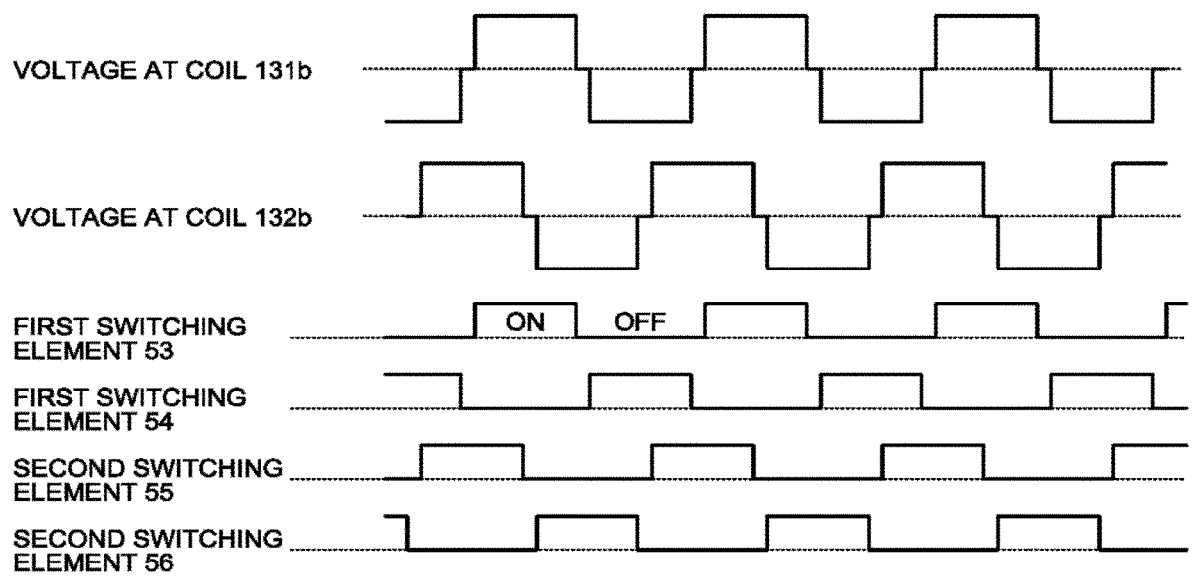
FIG. 7 is a timing chart illustrating a relation between the voltages applied to the coils in the second X-ray tube, and ON/OFF of the switching elements in the first embodiment.

A method by which the anode-rotating coil driver 5 according to the first embodiment drives the second X-ray tube 13b will now be explained with reference to FIG. 7. FIG. 7 is a timing chart illustrating a relation between the voltages applied to the coils in the second X-ray tube, and ON/OFF of the switching elements, in the first embodiment. With this method, the switching element driving circuitry 59 controls the ON and OFF of the switching elements so that the two-phase alternating current is generated by the single-phase half bridge inverter circuit. As to the matters that are the same as those in the method by which the anode-rotating coil driver 5 according to the first embodiment drives the first X-ray tube 13a, as explained with reference to FIG. 5, explanations of such matters will be omitted.

The three-phase alternating current power source AC4 supplies a three-phase alternating current at an effective voltage of 400 V to the three-phase rectifier diode bridge 41. The three-phase rectifier diode bridge 41 full-wave rectifies the three-phase alternating current, and applies 560-V direct-current voltage to the smoothing capacitor 42. The 560-V direct-current voltage is the peak voltage of the three-phase alternating current that is supplied from the three-phase alternating current power source AC4 to the three-phase rectifier diode bridge 41. The smoothing capacitor 42 applies the 560-V direct-current voltage to the capacitor 521 and the capacitor 522. In other words, the AC/DC converter circuitry 4 generates 560-V direct-current voltage, and applies the voltage to the capacitor 521 and the capacitor 522. In this manner, a 280-V direct-current voltage is applied to each of the capacitor 521 and the capacitor 522.

The switching element driving circuitry 59 supplies a voltage pulse to the first switching element 53, the first switching element 54, the second switching element 55 and the second switching element 56. In this manner, the switching element driving circuitry 59 switches the first switching element 53, the first switching element 54, the second switching element 55, and the second switching element 56 to ON or OFF at the timing illustrated in FIG. 7, for example.

When the first switching element 53 is ON and the first switching element 54 is OFF, a +280-V voltage with reference to the common terminal 13c is applied to the coil 131b. This +280-V voltage is the 280-V voltage applied to the capacitor 521. When the first switching element 53 is OFF and the first switching element 54 is ON, a −280-V voltage with reference to the common terminal 13c is applied to the coil 131b. The −280-V voltage is the 280-V voltage applied to the capacitor 522. By switching the first switching element 53 and the first switching element 54 to ON alternatingly at a constant cycle, the switching element driving circuitry 59 supplies a rectangular wave alternating current illustrated in FIG. 7 to the coil 131b. The voltage applied to the coil 131b is also referred to as a phase voltage.

When the second switching element 55 is ON and the second switching element 56 is OFF, a +280-V voltage with reference to the common terminal 13c is applied to the coil 132b. This +280-V voltage is the 280-V voltage applied to the capacitor 521. When the second switching element 55 is OFF and the second switching element 56 is ON, a −280-V voltage with reference to the common terminal 13c is applied to the coil 132b. This −280-V voltage is the 280-V voltage applied to the capacitor 522. By switching the second switching element 55 and the second switching element 56 to ON alternatingly at a constant cycle, the switching element driving circuitry 59 supplies the rectangular wave alternating current illustrated in FIG. 7 to the coil 132b. The voltage applied to the coil 132b is also referred to as a phase voltage.

The rectangular wave alternating current supplied to the coil 132b and the rectangular wave alternating current supplied to the coil 131b have the same cycle. The switching element driving circuitry 59, however, adds a delay of ¼ of the cycle of the rectangular wave alternating current to the timing at which the second switching element 55 and the second switching element 56 are switched to ON alternatingly, with respect the timing at which the first switching element 53 and the first switching element 54 are switched to ON alternatingly. Therefore, the rectangular wave alternating current supplied to the coil 132b is shifted by 90 degrees with respect to the phase of the rectangular wave alternating current supplied to the coil 131b. With this phase difference, the coil 131b and the coil 132b generate a rotating magnetic field. This rotating magnetic field causes the anode 130b to rotate.

During the period from when the first switching element 53 is switched to OFF to when the first switching element 54 is switched to ON, and during the period from when the first switching element 54 is switched to OFF to when the first switching element 53 is switched to ON, the first switching element 53 and the first switching element 54 are both OFF. During these periods, the voltage applied to the coil 131b and the coil 132b becomes zero. This is to prevent the anode-rotating coil driver 5 from failing due to the first switching element 53 and the first switching element 54 both being switched to ON simultaneously. The period in which the first switching element 53 and the first switching element 54 are switched to OFF is also referred to as deadtime. The same applies to the second switching element 55 and the second switching element 56. The third switching element 57 and the third switching element 58 always remain OFF.

In the explanation above, the AC/DC converter circuitry 4 is supplied with the three-phase alternating current at an effective voltage of 400 V from the three-phase alternating current power source AC4. Alternatively, there are cases in which the X-ray high-voltage device 3 is input with a three-phase alternating current at an effective voltage of 200 V, in addition to being input with a three-phase alternating current at an effective voltage of 400 V. Explained now are examples in which the X-ray high-voltage device 3 drives the first X-ray tube 13a and in which the X-ray high-voltage device 3 drives the second X-ray tube 13b, with an input of the three-phase alternating current at an effective voltage of 200 V.

Figure 8:
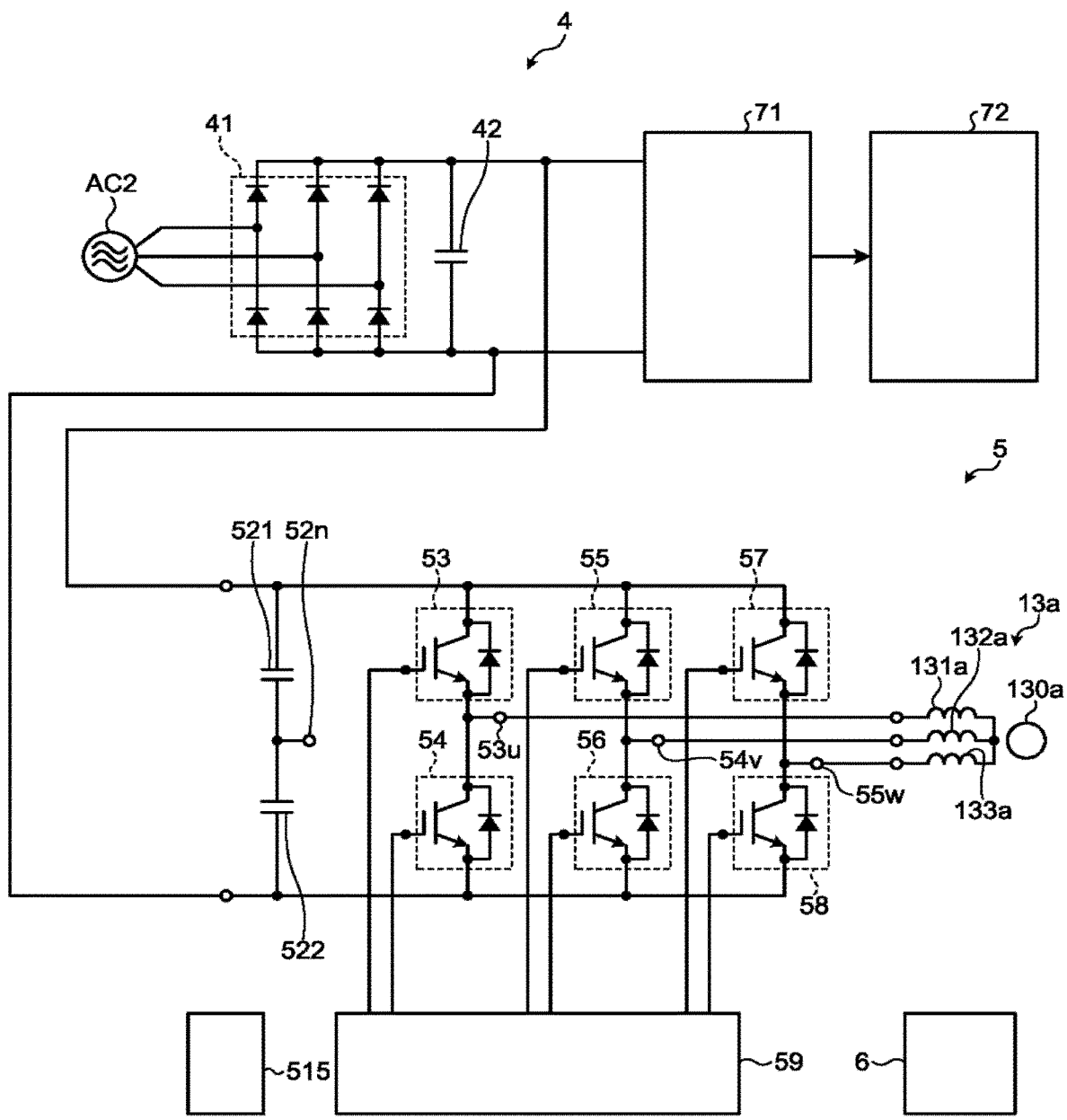
FIG. 8 is a schematic illustrating another exemplary circuit configuration of the anode-rotating coil driver according to the first embodiment at the time when the anode-rotating coil driver supplies a three-phase alternating current to the first X-ray tube.

To begin with, an example in which the anode-rotating coil driver 5 drives the first X-ray tube 13a with an input of a three-phase alternating current at an effective voltage of 200 V will now be explained in detail with reference to FIG. 8. FIG. 8 is a schematic illustrating another exemplary circuit configuration of the anode-rotating coil driver according to the first embodiment at the time when the anode-rotating coil driver supplies the three-phase alternating current to the first X-ray tube.

The three-phase rectifier diode bridge 41 is connected to a three-phase alternating current power source AC2. The three-phase alternating current power source AC2 supplies a three-phase alternating current at an effective voltage of 200 V to the three-phase rectifier diode bridge 41. The smoothing capacitor 42 outputs a 280-V direct-current voltage to the anode-rotating coil driver 5.

To cause the first X-ray tube 13a to emit X-rays, the X-ray tube switching circuitry 6 performs the same control as that when the input is the three-phase alternating current at an effective voltage of 400 V. In other words, to cause the first X-ray tube 13a to emit X-rays, the X-ray tube switching circuitry 6 supplies power to the first X-ray tube 13a via the first inter-switching-element terminal 53u, the second inter-switching-element terminal 54v, and the third inter-switching-element terminal 55w. For example, to cause the first X-ray tube 13a to emit X-rays, the X-ray tube switching circuitry 6 switches the first switch group 611 illustrated in FIG. 4 to ON, and switches the second switch group 612 illustrated in FIG. 4 to OFF. As a result, the anode-rotating coil driver 5 comes to have a configuration with a three-phase full-bridge inverter circuit that uses the three sets of "two switching elements", as illustrated in FIG. 8, as the starter of the anode 130a, in the same manner as that illustrated in FIG. 3.

Because the first X-ray tube 13a is driven by the three-phase full-bridge inverter circuit, it is not necessary to step up or down the 280-V direct-current voltage output from the smoothing capacitor 42. In such a case, the step-up/step-down switching circuitry 515 connects the high-voltage-side terminal of the AC/DC converter circuitry 4 (the highvoltage-side terminal of the smoothing capacitor 42) to the high-voltage-side terminal of the two capacitors 521 and 522 (the high-voltage-side terminal of the capacitor 521), and connects the low-voltage-side terminal of the AC/DC converter circuitry 4 (the low-voltage-side terminal of the smoothing capacitor 42) to the low-voltage-side terminal of the two capacitors 521 and 522 (the low-voltage-side terminal of the capacitor 522). The way in which the anode-rotating coil driver 5 drives the first X-ray tube 13a is the same as that explained with reference to FIG. 5.

Figure 9:
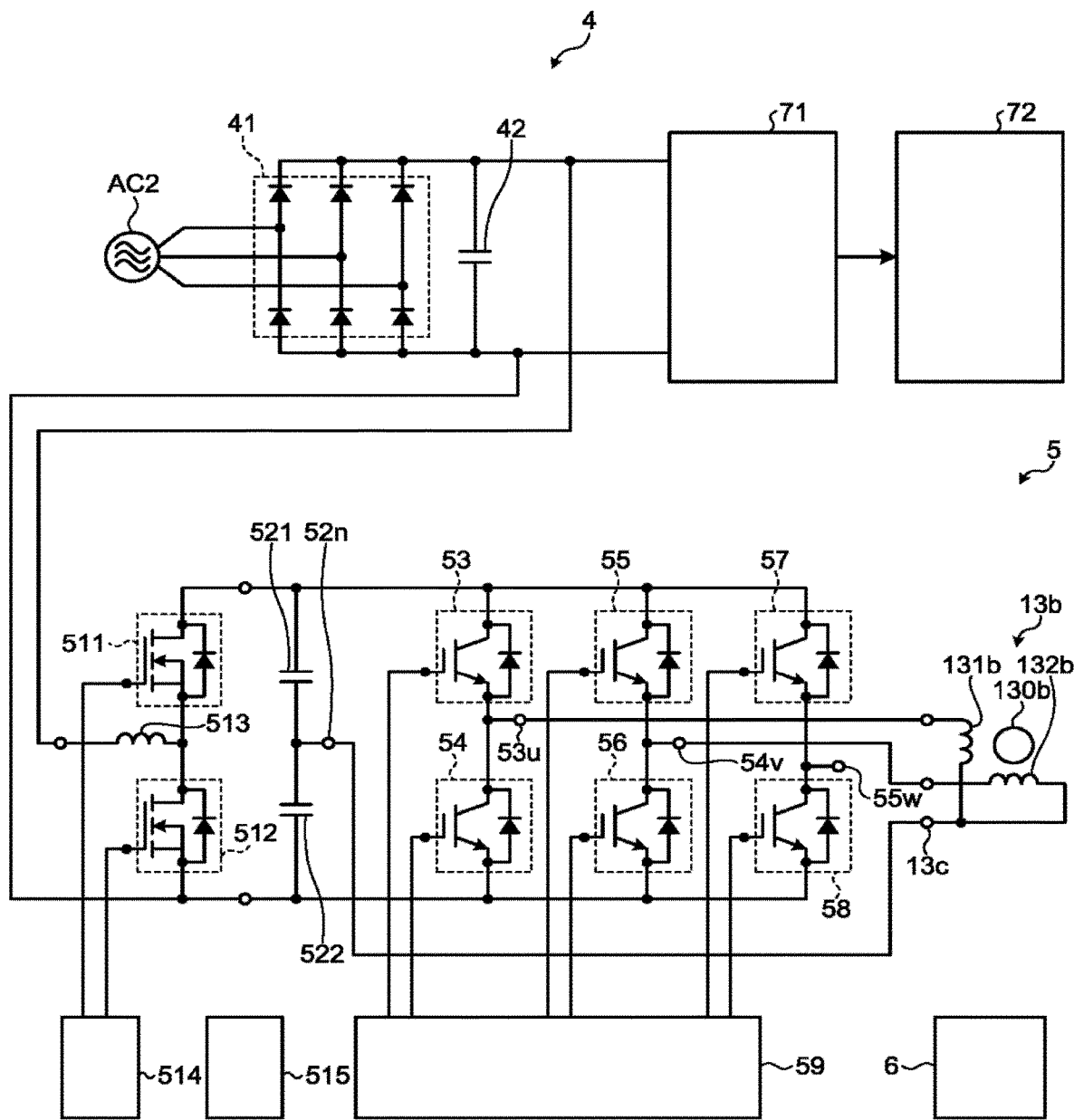
FIG. 9 is a schematic illustrating another exemplary circuit configuration of the anode-rotating coil driver according to the first embodiment at the time when the anode-rotating coil driver supplies a two-phase alternating current to the second X-ray tube.

An example in which the anode-rotating coil driver 5 drives the second X-ray tube 13b with an input of the three-phase alternating current at an effective voltage of 200 V will now be explained in detail with reference to FIG. 9. FIG. 9 is a schematic illustrating another exemplary circuit configuration of the anode-rotating coil driver according to the first embodiment at the time when the anode-rotating coil driver supplies a two-phase alternating current to the second X-ray tube.

To cause the second X-ray tube 13b to emit X-rays, the X-ray tube switching circuitry 6 performs the same control as that when the input is a three-phase alternating current at an effective voltage of 400 V. In other words, to cause the second X-ray tube 13b to emit X-rays, the X-ray tube switching circuitry 6 supplies power to the second X-ray tube 13b using the inter-capacitor terminal 52n, and two of the first inter-switching-element terminal 53u, the second inter-switching-element terminal 54v, and the third inter-switching-element terminal 55w. For example, to cause the second X-ray tube 13b to emit X-rays, the X-ray tube switching circuitry 6 switches the first switch group 611 illustrated in FIG. 4 to OFF, and switches the second switch group 612 illustrated in FIG. 4 to ON. As a result, the anode-rotating coil driver 5 comes to have a configuration with a single-phase half bridge inverter circuit that uses a neutral point (the inter-capacitor terminal 52n) and two sets of "two switching elements", as illustrated in FIG. 9, as the starter of the anode 130b, in the same manner as that illustrated in FIG. 6.

Because the second X-ray tube 13b is driven by the single-phase half bridge inverter circuit, it is necessary to step up the 280-V direct-current voltage output from the smoothing capacitor 42 to 560-V direct-current voltage. In the first embodiment, the step-up/step-down converter including the n-type MOSFET 511, the n-type MOSFET 512, the step-up/step-down coil 513, the step-up/step-down switching element driving circuitry 514, and the step-up/step-down switching circuitry 515 is also used in stepping up the voltage.

Specifically, to step up the voltage, the step-up/step-down switching circuitry 515 connects the low-voltage-side terminal of the step-up/step-down converter (the source of the n-type MOSFET 512) to the low-voltage-side terminal of the AC/DC converter circuitry 4 (the low-voltage-side terminal of the smoothing capacitor 42), and to the low-voltage-side terminal of the two capacitors 521 and 522 (the low-voltage-side terminal of the capacitor 522), as illustrated in FIG. 9, in the same manner as when the voltage is stepped down. To step up the voltage, the step-up/step-down switching circuitry 515 connects the high-voltage-side terminal of the step-up/step-down converter (the drain of the n-type MOSFET 511) to the high-voltage-side terminal of the two capacitors 521 and 522 (the high-voltage-side terminal of the capacitor 521), as illustrated in FIG. 9. To step up the voltage, the step-up/step-down switching circuitry 515 also connects the other end of the step-up/step-down coil 513 to the high-voltage-side terminal of the AC/DC converter circuitry 4 (the high-voltage-side terminal of the smoothing capacitor 42), as illustrated in FIG. 9.

In other words, the step-up/step-down switching circuitry 515 swaps the input and the output of "the circuit including the n-type MOSFET 511, the n-type MOSFET 512, and the step-up/step-down coil 513", from those in the configuration illustrated in FIG. 3. Specifically, the step-up/step-down switching circuitry 515 reconnects the other end of the step-up/step-down coil 513 from the high-voltage-side terminal of the capacitor 521 to the high-voltage-side terminal of the smoothing capacitor 42, and reconnects the drain of the n-type MOSFET 511 from the high-voltage-side terminal of the smoothing capacitor 42 to the high-voltage-side terminal of the capacitor 521.

In this manner, the step-up/step-down converter functions as a step-up converter, and steps up the 280-V direct-current voltage generated by the AC/DC converter circuitry 4, and applies the resultant voltage to the capacitor 521 and the capacitor 522. The step-up/step-down converter operates in the manner described below, for example.

The step-up/step-down switching element driving circuitry 514 supplies a voltage pulse to the gate of the n-type MOSFET 511 and the gate of the n-type MOSFET 512, to switch the n-type MOSFET 511 and the n-type MOSFET 512 to ON alternatingly at a constant cycle. In this example, the n-type MOSFET 511 and the n-type MOSFET 512 are switched to ON alternatingly at a duty ratio of approximately 0.5. As a result, the step-up/step-down converter steps up the 280-V direct-current voltage applied between the other end of the step-up/step-down coil 513 and the source of the n-type MOSFET 512 to 560 V. The relation between these voltages and the duty ratio is expressed by the following Equation, where Vin denotes the 280-V direct-current voltage applied between the other end of the step-up/step-down coil 513 and the source of the n-type MOSFET 512, and Vout denotes the 560-V direct-current voltage output from the step-up/step-down converter.

$$Vout = \frac{1}{1-D} \cdot Vin = \frac{1}{1-0.5} \times 280 = 560$$

The way in which the anode-rotating coil driver 5 drives the second X-ray tube 13b is the same as that explained with reference to FIG. 7.

As described above, the anode-rotating coil driver 5 according to the first embodiment can generate both of the two-phase alternating current and the three-phase alternating current, with only one device. In other words, the anode-rotating coil driver 5 can implement both of the three-phase full-bridge inverter circuit and the single-phase half bridge inverter circuit by switching the connections in one circuit including "the capacitor 521 and the capacitor 522, and three sets of two switching elements (the first switching elements 53 and 54, the second switching elements 55 and 56, and the third switching elements 57 and 58)". As a result, the anode-rotating coil driver 5 can supply a three-phase alternating current to the first X-ray tube 13a using the three-phase full-bridge inverter circuit, so that the rotation of the anode 130a can be available quickly at an appropriate timing. Therefore, the first image acquisition apparatus 10a can acquire an X-ray image at an appropriate timing.

Furthermore, because the anode-rotating coil driver 5 can supply a two-phase alternating current to the second X-ray tube 13b using the single-phase half bridge inverter circuit, a restriction of the output voltage pulse width, which has been performed when the two-phase alternating current is generated using a three-phase inverter, is no longer necessary. Therefore, the rotation of the anode 130b can be available quickly at an appropriate timing. Therefore, the second image acquisition apparatus 10b can acquire an X-ray image at an appropriate timing. Furthermore, the isolation transformer, which has been required to prevent an arm short circuit when a two-phase alternating current is generated using a three-phase inverter, is not required in the configuration according to the embodiment.

Figure 10:
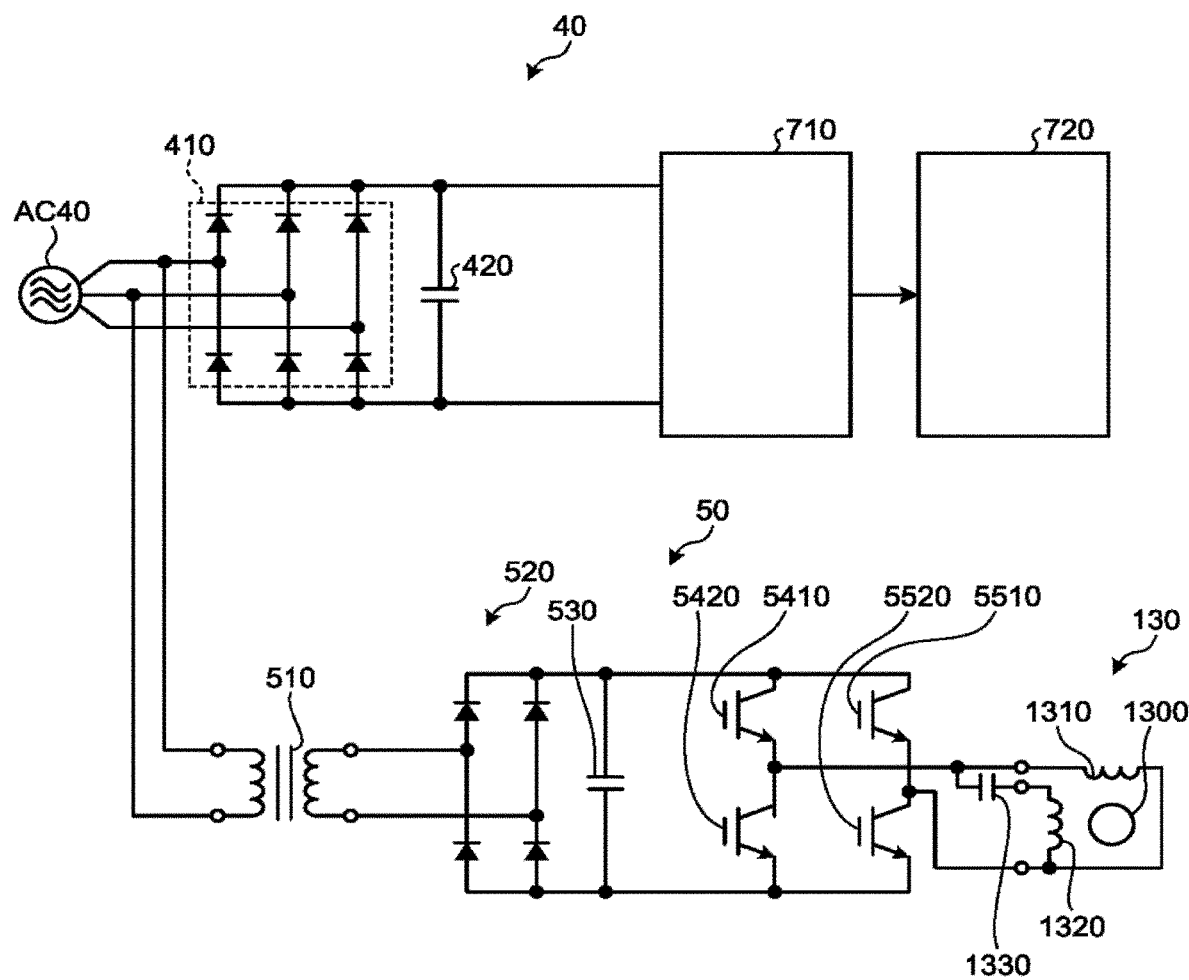
FIG. 10 is a schematic illustrating a comparative example in the first embodiment.

Furthermore, because the anode-rotating coil driver 5 uses a rectified/smoothed direct-current voltage as a power source to be supplied to the high-voltage generating inverter circuitry 71, and is provided with a step-up/step-down converter, both of the first X-ray tube 13a and the second X-ray tube 13b can be driven regardless of whether the effective voltage of the alternating current voltage supplied by the three-phase alternating current power source AC is 400 V or 200 V. Furthermore, according to the first embodiment, use of such a configuration can suppress the increases in size and weight. This advantageous effect will now be explained using a comparative example illustrated in FIG. 10. FIG. 10 is a schematic illustrating a comparative example in the first embodiment.

In the comparative example illustrated in FIG. 10, an X-ray tube 130 is an X-ray tube in which an anode 1300 is driven by a single-phase alternating current, and includes a coil 1310 and a coil 1320, and a phase advancing capacitor 1330. The coil 1310 and the coil 1320 require a supply of an alternating current at an effective voltage of 200 V. An AC/DC converter circuitry 40 illustrated in FIG. 10 includes a three-phase rectifier diode bridge 410 and a smoothing capacitor 420, and is connected to a three-phase alternating current power source AC40. The three-phase alternating current power source AC40 generates a three-phase alternating current at an effective voltage of 400 V. The three-phase rectifier diode bridge 410 full-wave rectifies the three-phase alternating current supplied from the three-phase alternating current power source AC40, and applies the direct-current voltage to the capacitor 420. A high-voltage generating inverter circuitry 710 converts the direct-current voltage applied to the capacitor 420 into an alternating current voltage, and supplies the alternating current voltage to a high-voltage generator 720. The high-voltage generator 720 converts and steps up the alternating current voltage into a direct-current voltage, and applies the resultant voltage to the X-ray tube 130 as the tube voltage.

An anode-rotating coil driver 50 illustrated in FIG. 10 includes a transformer 510, a diode bridge 520, a capacitor 530, an IGBT 5410, an IGBT 5420, an IGBT 5510, and an IGBT 5520. The transformer 510 is connected to two of the three output terminals of the three-phase alternating current power source AC40, and converts the alternating current at an effective voltage of 400 V into an alternating current at an effective voltage of 200 V. The transformer 510 supplies the alternating current at an effective voltage of 200 V to the anode-rotating coil driver 50. The diode bridge 520 full-wave rectifies the alternating current supplied by the transformer 510, and applies the direct-current voltage to the capacitor 530. A state in which the IGBT 5410 and the IGBT 5520 are ON and a state in which the IGBT 5420 and the IGBT 5510 are ON are repeated alternatingly at a constant cycle, the anode-rotating coil driver 50 supplies the single-phase alternating current to the X-ray tube 130.

The single-phase alternating current output from the anode-rotating coil driver 50 is supplied to the coil 1310 and the coil 1320. The phase advancing capacitor 1330 connected to the coil 1320, however, advances the phase of the single-phase alternating current by 90 degrees. Therefore, the alternating current flowing through the coil 1310 has a phase that is 90 degrees behind from that of the alternating current flowing through the coil 1320. With this phase difference, the coil 1310 and the coil 1320 generate a rotating magnetic field. This rotating magnetic field causes the anode 1300 to rotate.

However, because the comparative example illustrated in FIG. 10 is provided with the phase advancing capacitor 1330, the weight and the size are increased, disadvantageously. Furthermore, in the comparative example illustrated in FIG. 10, when the effective voltage of the alternating current supplied by the three-phase alternating current power source is 400 V, the comparative example requires the transformer 510 for converting the three-phase alternating current to the three-phase alternating current at the effective voltage of 200 V, and therefore, the weight and the size are increased further.

By contrast, the anode-rotating coil driver 5 according to the first embodiment does not require the transformer 510 illustrated in FIG. 10. Furthermore, the second X-ray tube 13b does not require the phase advancing capacitor 1330, unlike the X-ray tube 130 illustrated in FIG. 10. Therefore, in the first embodiment, increases in the weight and the size can be suppressed. Furthermore, the anode-rotating coil driver 5 can not only step down the voltage but also step up the voltage using the same circuit, merely by swapping the connections to the input and the output of "the circuit including the n-type MOSFET 511, the n-type MOSFET 512, and the step-up/step-down coil 513".

In the X-ray diagnosis system 1 described above, to drive the first X-ray tube 13a using a three-phase alternating current at an effective voltage of 400 V as an input, it is necessary to step down the inverter input voltage from 560 V to 280 V. To drive the second X-ray tube 13b using a three-phase alternating current at an effective voltage of 200 V as an input, it is necessary to step up the inverter input voltage from 280 V to 560 V. By contrast, to drive the first X-ray tube 13a using a three-phase alternating current at an effective voltage of 200 V as an input, and to drive the second X-ray tube 13b using a three-phase alternating current at an effective voltage of 400 V as an input, there is no need for stepping up or stepping down the voltage. Therefore, in the first embodiment, the anode-rotating coil driver 5 is enabled to switch to a configuration in which "the step-up/step-down converter that is capable of stepping up and stepping down the voltage by swapping the input and the output" is inserted between the AC/DC converter circuitry 4 and the two capacitors 521 and 522, and to a configuration in which the step-up/step-down converter is not inserted.

The effective voltage of the voltage to be applied may also be stepped down to 200 V through the control of the inverter circuitry, without using a step-down converter. Some examples of such a method include a method that shortens the time for which the switching elements in the inverter circuitry are ON, and a method that modulates an ON signal for switching the switching elements in the inverter circuitry to ON, with a carrier frequency that is higher than the frequency of the alternating current voltage to be applied to the coils in the X-ray tube (the coils 131a, 132a, 133a in the first X-ray tube 13a). However, because these methods are incapable of stepping up the voltage, to drive the second X-ray tube 13b using a three-phase alternating current at an effective voltage of 200 V as an input, a step-up converter will be required before the inverter. In such a case, because the only function required is step-up, a circuit (step-up converter) with a simpler configuration, compared with the step-up/step-down converter explained in the first embodiment, may be provided.

Figure 11:
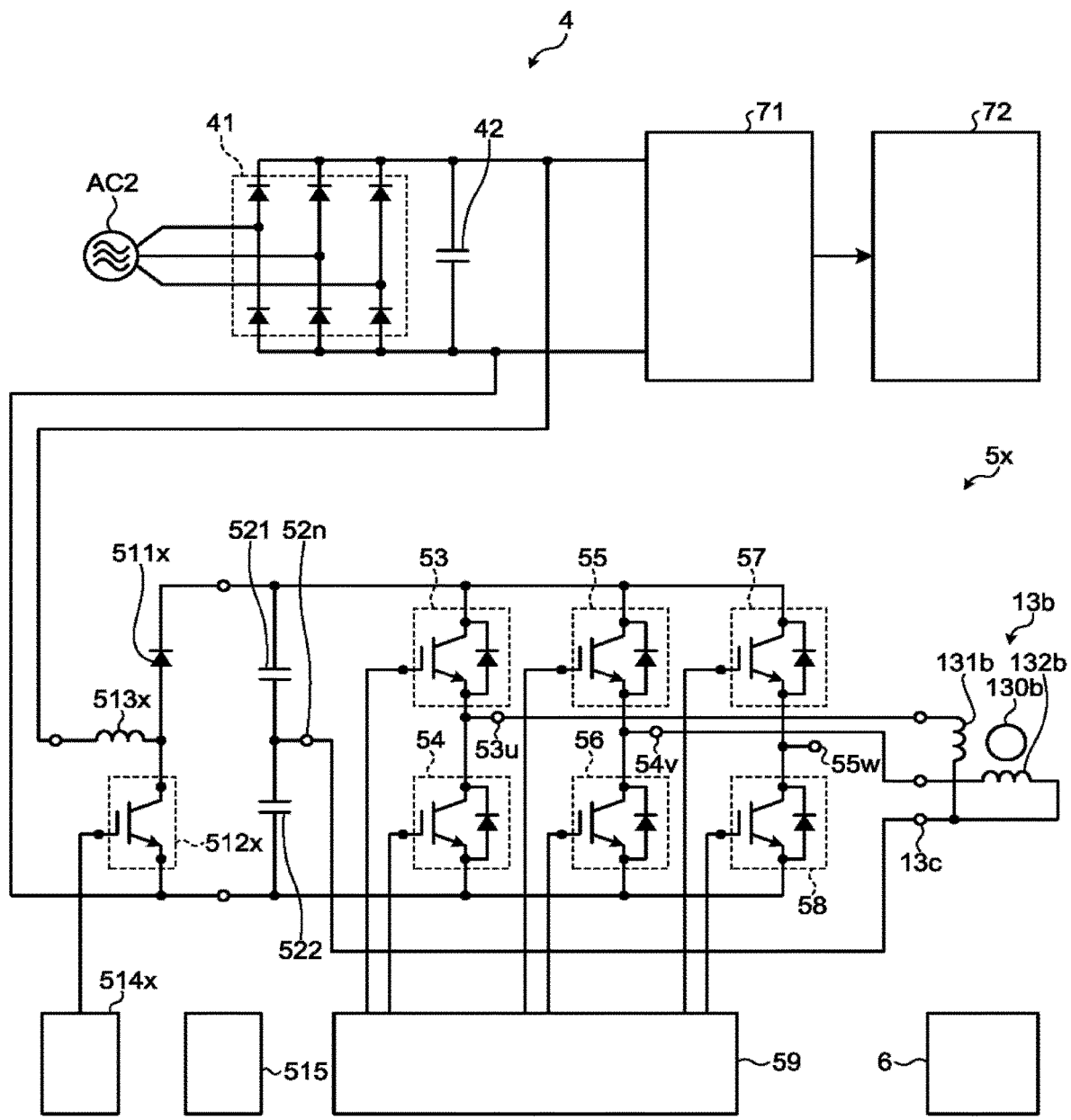
FIG. 11 is a schematic illustrating an exemplary circuit configuration of an anode-rotating coil driver according to a second embodiment.
Figure 12:
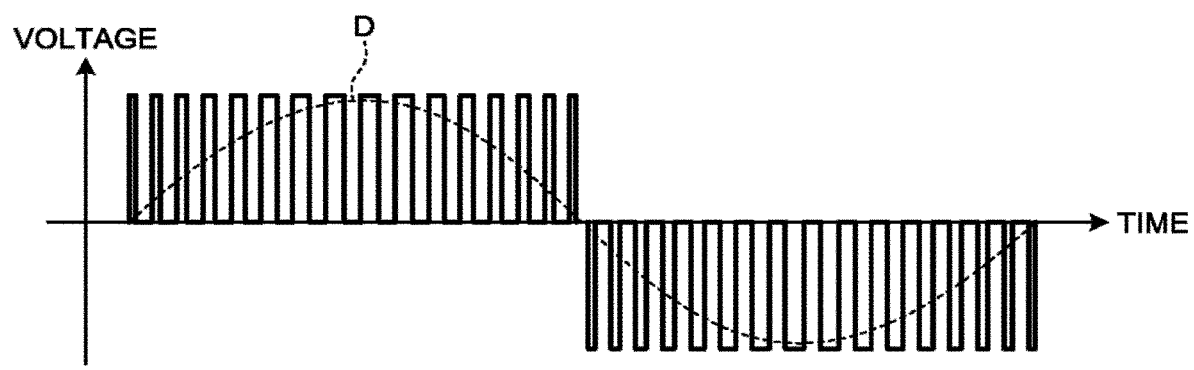
FIG. 12 is a schematic for explaining PWM control performed by switching element driving circuitry.

In a second embodiment, the configuration in which only the step-up converter is arranged will be explained. In the second embodiment as well, the X-ray tube switching circuitry 6 switches the connections in the same manner as in the first embodiment. FIG. 11 illustrates an example of an anode-rotating coil driver 5x having only the step-up converter. FIG. 11 is a schematic illustrating an exemplary circuit configuration of the anode-rotating coil driver according to the second embodiment. FIG. 11 illustrates an exemplary circuit configuration of the anode-rotating coil driver 5x at the time when the second X-ray tube 13b is caused to emit X-rays using the three-phase alternating current power source AC2 that supplies a three-phase alternating current at an effective voltage of 200 V as a power source. The anode-rotating coil driver 5x includes a diode 511x, an IGBT 512x, a step-up coil 513x, and step-up switching element driving circuitry 514x, instead of the n-type MOSFET 511, the n-type MOSFET 512, the step-up/step-down coil 513, and the step-up/step-down switching element driving circuitry 514 described above. "The diode 511x, the IGBT 512x, the step-up coil 513x, and the step-up switching element driving circuitry 514x" is also referred to as a step-up converter. The IGBT 512x is also referred to as a step-up switching element.

In the step-up converter, the anode of the diode 511x and one end (collector) of the IGBT 512x are connected to one end of the step-up coil 513x. In the second embodiment, the step-up/step-down switching circuitry 515 is a step-up switching circuit, and switches to a configuration in which the step-up converter steps up the direct-current voltage, and to a configuration in which the step-up converter does not step up the direct-current voltage.

When the direct-current voltage is to be stepped up, the step-up/step-down switching circuitry 515 connects the cathode of the diode 511x to the high-voltage-side terminal of the two capacitors (the high-voltage-side terminal of the capacitor 521). Furthermore, when the direct-current voltage is to be stepped up, the step-up/step-down switching circuitry 515 connects the other end (emitter) of the IGBT 512x to the low-voltage-side terminal of the AC/DC converter circuitry 4 (the low-voltage-side terminal of the smoothing capacitor 42) and the low-voltage-side terminal of the two capacitors (the high-voltage-side terminal of the capacitor 522). Furthermore, when the direct-current voltage is to be stepped up, the step-up/step-down switching circuitry 515 connects the other end of the step-up coil 513x to the high-voltage-side terminal of the AC/DC converter circuitry 4 (high-voltage-side terminal of the smoothing capacitor 42).

In this manner, the step-up converter is inserted between the AC/DC converter circuitry 4 and the two capacitors (521, 522), and applies the voltage resultant of stepping up the direct-current voltage to the two capacitors (521, 522). The step-up switching element driving circuitry 514x supplies a voltage pulse to the step-up switching element. In other words, the step-up switching element driving circuitry 514x supplies a voltage pulse to the gate of the IGBT 512x, and switches the IGBT 512x to ON/OFF at a duty ratio of approximately 0.5 (50%). In this manner, the step-up converter steps up the 280-V direct-current voltage applied between the one end of the step-up coil 513x and the emitter of the IGBT 512x to 560 V.

When the voltage is not to be stepped up, the step-up/step-down switching circuitry 515 connects the AC/DC converter circuitry 4 to the two capacitors (521, 522) not via the step-up converter. Specifically, the step-up/step-down switching circuitry 515 connects the high-voltage-side terminal of the smoothing capacitor 42 to the high-voltage-side terminal of the capacitor 521, and connects the low-voltage-side terminal of the smoothing capacitor 42 to the low-voltage-side terminal of the capacitor 522.

Through this operation, to drive the first X-ray tube 13a using a three-phase alternating current at an effective voltage of 200 V as an input, the anode-rotating coil driver 5x comes to have a circuit configuration illustrated in FIG. 6. Furthermore, to drive the second X-ray tube 13b using a three-phase alternating current at an effective voltage of 400 V as an input, the anode-rotating coil driver 5x comes to have the configuration illustrated in FIG. 9.

In the second embodiment, to drive the first X-ray tube 13a using a three-phase alternating current at an effective voltage of 400 V as an input, the anode-rotating coil driver 5x comes to have the configuration illustrated in FIG. 6. In such a case, the effective voltage to be applied to the three-phase full-bridge inverter circuit is brought down to 200 V by causing the switching element driving circuitry 59 to execute processes such as a process for shortening the ON time or a modulation process described above. In this manner, the first X-ray tube 13a can be driven.

The embodiments may be implemented in various different ways other than those described above.

In the embodiments described above, the anode-rotating coil driver 5 supplies the rectangular-wave alternating current illustrated in FIG. 5 to the coil 131a, the coil 132a, and the coil 133a included in the first X-ray tube 13a, and supplies the rectangular wave alternating current illustrated in FIG. 7 to the coil 131b and the coil 132b included in the second X-ray tube 13b. However, the embodiments are not limited thereto.

In the embodiments described above, the switching element driving circuitry 59 switches the first switching element 53, the first switching element 54, the second switching element 55, the second switching element 56, the third switching element 57, and the third switching element 58 to ON for a predetermined period at the timing illustrated in FIG. 5 or 7, but the embodiments are not limited thereto. The switching element driving circuitry 59 may switch ON/OFF of the IGBTs by performing pulse width modulation (PWM) during the predetermined period. FIG. 12 to FIG. 15 are schematics for explaining the PWM control performed by the switching element driving circuit. For example, the anode-rotating coil driver 5 can supply a pseudo-sine-wave alternating current to the coil 131a, the coil 132a, and the coil 133a in the first X-ray tube 13a or the coil 131b and the coil 132b in the second X-ray tube 13b, by performing the PWM control illustrated in FIG. 12. Furthermore, when the switching element driving circuitry 59 performs the pulse width modulation at fine granularity, the pseudo-sine-wave alternating current is brought closer to the sine-wave alternating current indicated by the dotted line D illustrated in FIG. 12, for example.

In an X-ray tube, the rotor of a motor is placed inside of the vacuum container of the X-ray tube, and the stator coil is disposed outside, with the outer wall of the container disposed between the stator and the rotor. Therefore, there is a great gap between the rotor and the stator. For this reason, even if an X-ray tube is driven by a rectangular waveform, a cogging phenomenon resultant of torque variation, which often occurs in a general motor, is less likely to occur. By generating a pseudo-sine-wave alternating current, the torque variation introduced between the anode 130a and the coils 131*a*, 132*a*, and 133*a*, and the torque variation introduced between and the anode 130*b* and the coils 131*b* and 132*b* are further reduced. Therefore, the anode-rotating coil driver 5 enables the anode 130*a* and the anode 130*b* to rotate smoothly, so that the vibrations or strange sound resultant of vibrations of the first X-ray tube 13*a* and the second X-ray tube 13*b* can be suppressed.

Figure 13:
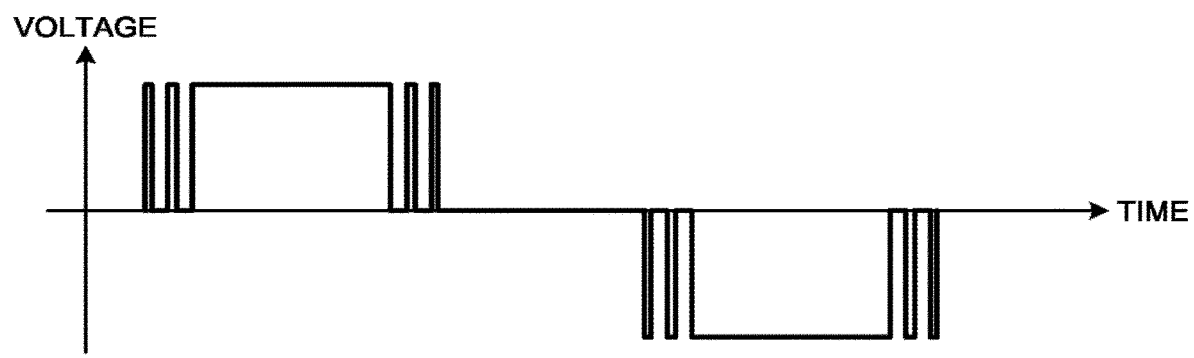
FIG. 13 is a schematic for explaining the PWM control performed by the switching element driving circuitry.
Figure 14:
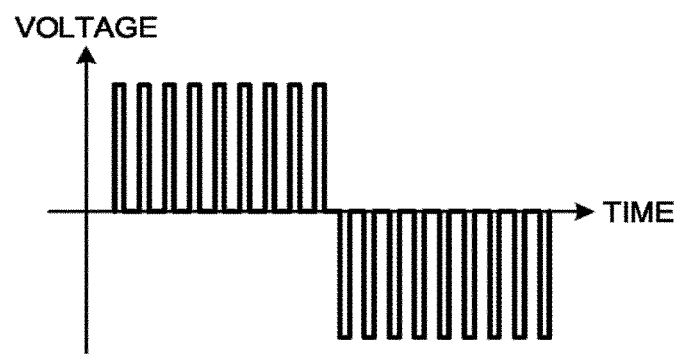
FIG. 14 is a schematic for explaining the PWM control performed by the switching element driving circuitry.
Figure 15:
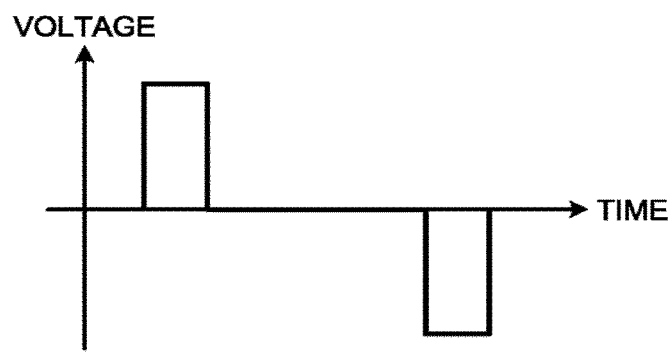
FIG. 15 is a schematic for explaining the PWM control performed by the switching element driving circuitry.

Furthermore, the switching element driving circuitry 59 can switch the IGBTs to ON/OFF by performing the pulse width modulation in the beginning and the end of a predetermined period, as illustrated in FIG. 13. In such a case as well, the anode-rotating coil driver 5 can suppress vibrations of the first X-ray tube 13*a* and the second X-ray tube 13*b*.

To start the rotation of the anode 130*a* or the anode 130*b*, or to increase the rotational speed of the anode 130*a* or the anode 130*b*, the anode-rotating coil driver 5 supplies alternating current power at an effective voltage of 200 V to the coil 131*a*, the coil 132*a*, and the coil 133*a* or the coil 131*b* and the coil 132*b*, for example. To maintain the current rotational speed of the anode 130*a* or the anode 130*b* after the rotational speed has been increased to a specified level, the anode-rotating coil driver 5 supplies an alternating current at an effective voltage 40 V to the coil 131*a*, the coil 132*a*, and the coil 133*a* or the coil 131*b* and the coil 132*b*, for example. In such a case, the anode-rotating coil driver 5 performs the PWM control illustrated in FIG. 14 or 15, for example. In the PWM control, the duty ratio is adjusted so that the effective voltage will become 40 V.

Figure 16:
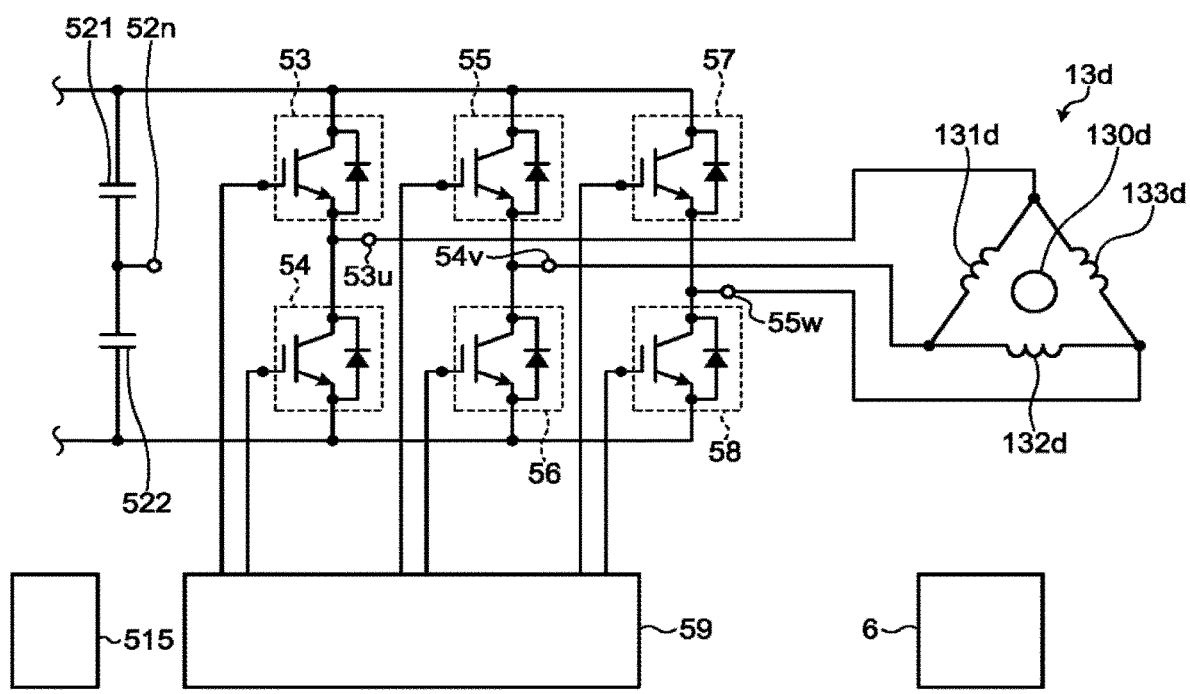
FIG. 16 is a schematic illustrating another example of the first X-ray tube.

In the embodiments described above, the first image acquisition apparatus 10*a* includes the first X-ray tube 13*a* in which the coil 131*a*, the coil 132*a*, and the coil 133*a* are connected in a star connection, but the embodiments are not limited thereto. FIG. 16 is a schematic illustrating another example of the first X-ray tube. The first image acquisition apparatus may also include, as illustrated in FIG. 16, a first X-ray tube 13*d* in which a coil 131*d*, a coil 132*d*, and a coil 133*d* are connected in a delta-connection. One end of the coil 131*d* is connected to the first inter-switching-element terminal 53*u*, and the other end of the coil 131*d* is connected to the second inter-switching-element terminal 54*v*. One end of the coil 132*d* is connected to the second inter-switching-element terminal 54*v*, and the other end of the coil 132*d* is connected to the third inter-switching-element terminal 55*w*. One end of the coil 133*d* is connected to the third inter-switching-element terminal 55*w*, and the other end of the coil 133*d* is connected to the first inter-switching-element terminal 53*u*. In this configuration, the anode-rotating coil driver 5 also uses the same method as that described above in the embodiments to cause the anode 130*d* in first X-ray tube 13*d* to rotate.

In the embodiments described above, the first X-ray tube 13*a* is included in the first image acquisition apparatus 10*a*, and the second X-ray tube 13*b* is included in the second image acquisition apparatus 10*b*, but the embodiments are not limited thereto. The first X-ray tube 13*a* and the second X-ray tube 13*b* may be included in one image acquisition apparatus.

Furthermore, explained in the embodiments described above is an example in which the X-ray diagnosis system 1 includes the first X-ray tube 13*a* and the second X-ray tube 13*b*. However, the embodiments are not limited thereto. For example, the X-ray diagnosis system 1 may include one of the first X-ray tube 13*a* and the second X-ray tube 13*b*.

Figure 17:
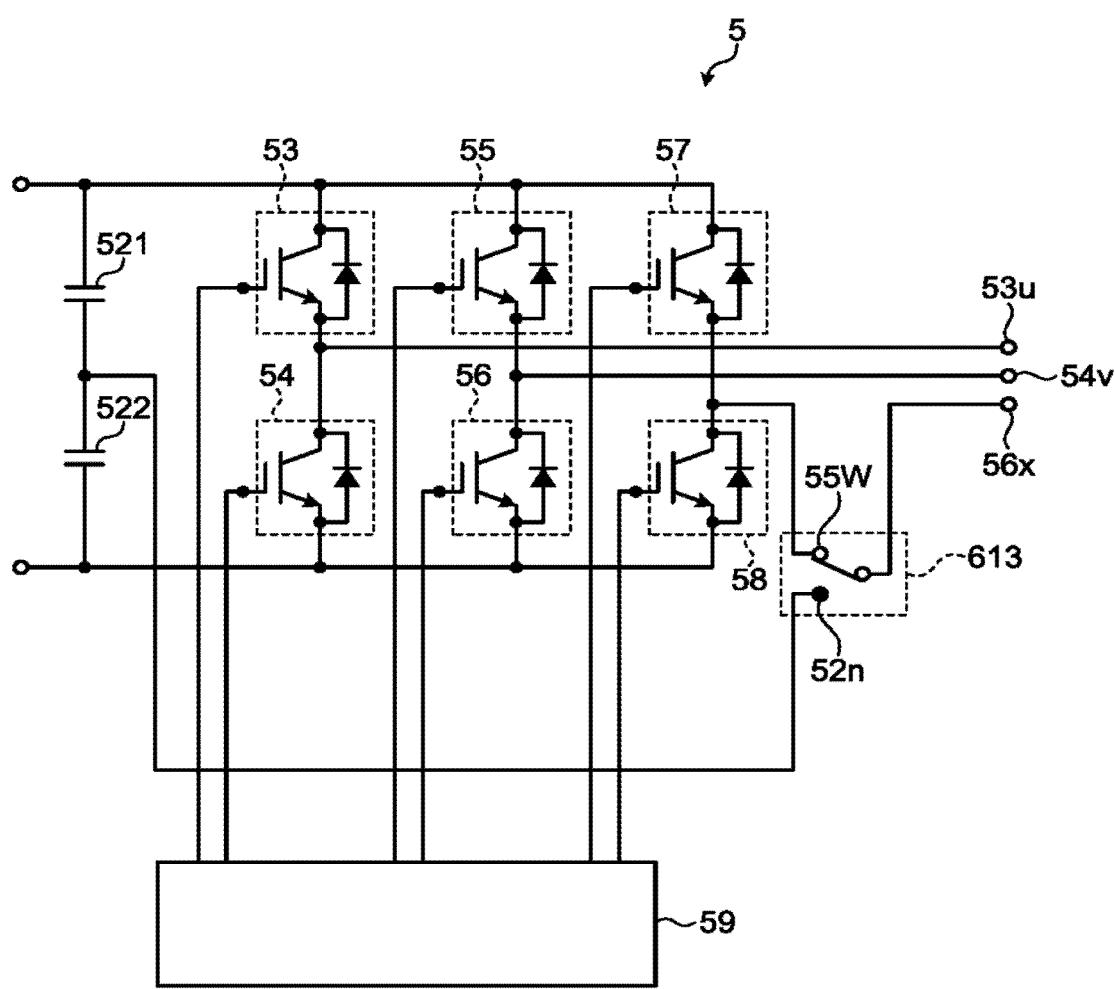
FIG. 17 is a schematic illustrating an exemplary circuit configuration of the anode-rotating coil driver.

For example, the anode-rotating coil driver 5 may include, as illustrated in FIG. 17, the first inter-switching-element terminal 53*u*, the second inter-switching-element terminal 54*v*, and a terminal 56*x*. A switch 613 may then be configured to connect the terminal 56*x* to one of the third inter-switching-element terminal 55*w* and the inter-capacitor terminal 52*n*. FIG. 17 is a schematic illustrating an exemplary circuit configuration of the anode-rotating coil driver 5.

Figure 18A:
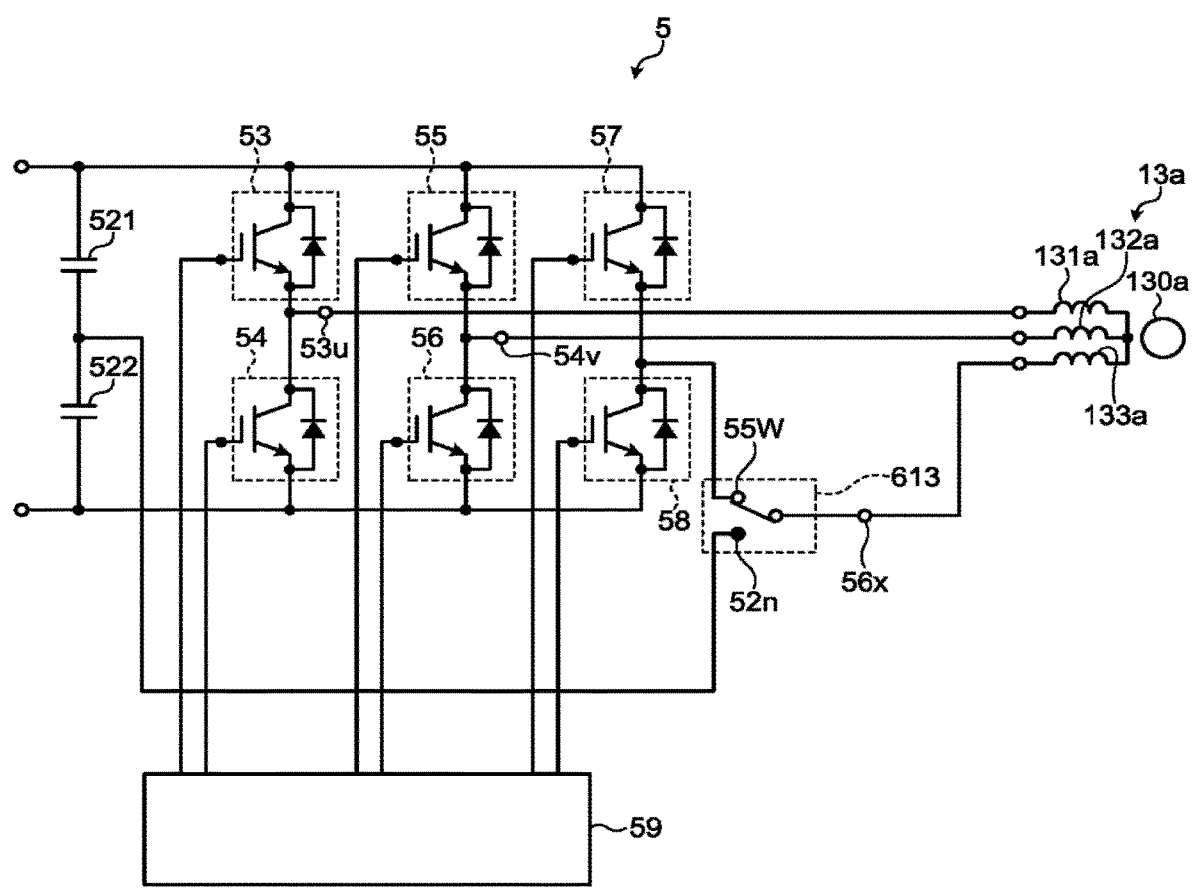
FIG. 18A is a schematic illustrating an exemplary circuit configuration of the anode-rotating coil driver.

As illustrated in FIG. 18A, when the X-ray diagnosis system 1 includes the first X-ray tube 13*a* only, the terminal 56*x* is connected to the third inter-switching-element terminal 55*w*. The first inter-switching-element terminal 53*u* is then connected to the coil 131*a* in the first X-ray tube 13*a*. The second inter-switching-element terminal 54*v* is connected to the coil 132*a* in the first X-ray tube 13*a*. The terminal 56*x*, which is connected to the third inter-switching-element terminal 55*w*, is connected to the coil 133*a* in the first X-ray tube 13*a*. The anode-rotating coil driver 5 then supplies the three-phase alternating current power to the first X-ray tube 13*a* via the first inter-switching-element terminal 53*u*, the second inter-switching-element terminal 54*v*, and the third inter-switching-element terminal 55*w*. FIG. 18A is a schematic illustrating an exemplary circuit configuration of the anode-rotating coil driver.

Figure 18B:
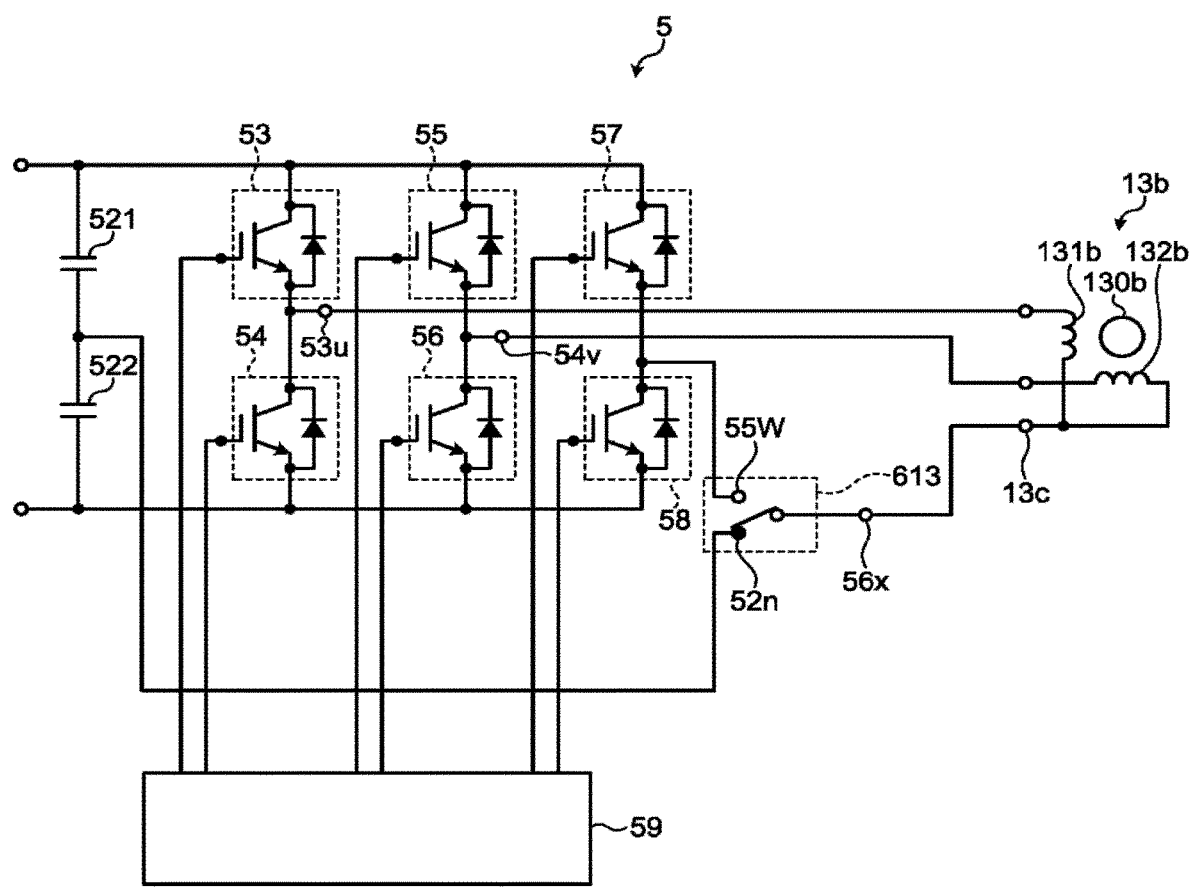
FIG. 18B is a schematic illustrating an exemplary circuit configuration of the anode-rotating coil driver.

By contrast, when the X-ray diagnosis system 1 includes the second X-ray tube 13*b* only as illustrated in FIG. 18B, the terminal 56*x* is connected to the inter-capacitor terminal 52*n*. The first inter-switching-element terminal 53*u* is connected to the coil 131*b* in the second X-ray tube 13*b*. The second inter-switching-element terminal 54*v* is connected to the coil 132*b* in the second X-ray tube 13*b*. The terminal 56*x*, which is connected to the inter-capacitor terminal 52*n*, is connected to the common terminal 13*c* in the second X-ray tube 13*b*. The anode-rotating coil driver 5 then supplies the two-phase alternating current power to the second X-ray tube 13*b* via the first inter-switching-element terminal 53*u*, the second inter-switching-element terminal 54*v*, and the inter-capacitor terminal 52*n*. FIG. 18B is a schematic illustrating an exemplary circuit configuration of the anode-rotating coil driver.

As described above, even when the X-ray diagnosis system 1 includes only one of the first X-ray tube 13*a* and the second X-ray tube 13*b*, the supply of the three-phase alternating current power and the supply of the two-phase alternating current power can be switched. For example, when an X-ray tube driven by three-phase alternating current power is replaced with an X-ray tube driven by two-phase alternating current power, the X-ray diagnosis system 1 can quickly enable either the X-ray tube before the replacement or the X-ray tube after the replacement.

Explained with reference to FIG. 4 is an example in which the supply of three-phase alternating current power and the supply of two-phase alternating current power are switched by controlling ON/OFF of the switch group 61. However, the embodiments are not limited thereto.

For example, the X-ray diagnosis system 1 includes the switch 613, as illustrated in FIG. 17, FIG. 18A, and FIG. 18B, instead of the switch group 61 illustrated in FIG. 4. The switch 613 is switched to a connection to the third inter-switching-element terminal 55*w*, and to a connection to the inter-capacitor terminal 52*n*. In other words, the switch 613 connects the coil 133*a* and the common terminal 13*c* to one of the third inter-switching-element terminal 55*w* and the inter-capacitor terminal 52*n*.

For example, the switch 613 connects the coil 133*a* to the third inter-switching-element terminal 55*w* as illustrated in FIG. 18A. In this configuration, the anode-rotating coil driver 5 supplies three-phase alternating current power to the first X-ray tube 13*a* via the first inter-switching-element terminal 53*u*, the second inter-switching-element terminal 54*v*, and the third inter-switching-element terminal 55*w*.

Alternatively, the switch 613 connects the common terminal 13c to the inter-capacitor terminal 52n as illustrated in FIG. 18B. In this configuration, the anode-rotating coil driver 5 supplies the two-phase alternating current power to the second X-ray tube 13b via the first inter-switching-element terminal 53u, the second inter-switching-element terminal 54v, and the inter-capacitor terminal 52n.

The switching of the switch 613 may be performed by the X-ray tube switching circuitry 6 or a user. For example, a user switches the connection to the terminal 56x from the third inter-switching-element terminal 55w to the inter-capacitor terminal 52n, by pressing a button provided to the X-ray diagnosis system 1. The user switches the connection to the terminal 56x from the inter-capacitor terminal 52n to the third inter-switching-element terminal 55w by pressing the button again. When the switch 613 is switched by a user, the X-ray diagnosis system 1 does not necessarily include the X-ray tube switching circuitry 6.

In the embodiments described above, the step-up/step-down converter includes the n-type MOSFET 511 and the n-type MOSFET 512, but the embodiments are not limited thereto. The step-up/step-down converter may include IGBTs, for example.

Examples of the processor described above include a central processing unit (CPU), a graphics processing unit (GPU), an application specific integrated circuit (ASIC), a programmable logic device (PLD), and a field programmable gate array (FPGA). Furthermore, examples of the PLD include a simple programmable logic device (SPLD) and a complex programmable logic device (CPLD).

In the embodiments described above, the functions of the collimator adjusting circuitry 11a, the collimator adjusting circuitry 11b, the driving circuitry 12a, the driving circuitry 12b, the generating circuitry 17a, the generating circuitry 17b, and the processing circuitry 25 are implemented by reading computer programs stored in the memory 24 and executing the computer program, but the embodiments are not limited thereto. Instead of storing a computer program in the memory 24, the computer program may be directly embedded in each of the circuitry. In such a configuration, each of the circuitry implements the function by reading the computer program directly embedded therein, and executing the computer program.

Each of the circuitry illustrated in FIG. 1 may be distributed or integrated as appropriate. For example, the processing circuitry 25 may be distributed to image acquisition control circuitry that implements the image acquisition control function 251, and to control circuitry that implements the control function 252. Furthermore, for example, the collimator adjusting circuitry 11a, the collimator adjusting circuitry 11b, the driving circuitry 12a, the driving circuitry 12b, the generating circuitry 17a, the generating circuitry 17b, and the processing circuitry 25 may be integrated into any units.

According to at least one of the embodiments explained above, it is possible to provide an X-ray diagnosis system and an anode-rotating coil driver capable of quickly enabling both of an X-ray tube driven by a two-phase alternating current and an X-ray tube driven by a three-phase alternating current, while suppressing increases in the weight and the size.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis system comprising:
an inter-capacitor terminal that is provided between two capacitors that are serially connected to each other;
a first inter-switching-element terminal that is provided between two first switching elements that are serially connected to each other;
a second inter-switching-element terminal that is provided between two second switching elements that are serially connected to each other; and
a third inter-switching-element terminal that is provided between two third switching elements that are serially connected to each other, wherein
the first inter-switching-element terminal, the second inter-switching-element terminal, and the third inter-switching-element terminal are configured to supply three-phase alternating current power, and the inter-capacitor terminal and two of the first inter-switching-element terminal, the second inter-switching-element terminal, and the third inter-switching-element terminal are configured to supply two-phase alternating current power.

2. The X-ray diagnosis system according to claim 1, further comprising switching circuitry configured to switch to connect the first inter-switching-element terminal, the second inter-switching-element terminal, and the third inter-switching-element terminal, and to connect the inter-capacitor terminal and the two of the first inter-switching-element terminal, the second inter-switching-element terminal, and the third inter-switching-element terminal.

3. The X-ray diagnosis system according to claim 1, wherein a three-phase full-bridge inverter circuit is formed by connecting the first inter-switching-element terminal, the second inter-switching-element terminal, and the third inter-switching-element terminal to three respective coils included in a first X-ray tube that is driven by three-phase alternating current power.

4. The X-ray diagnosis system according to claim 2, wherein a three-phase full-bridge inverter circuit is formed by connecting the first inter-switching-element terminal, the second inter-switching-element terminal, and the third inter-switching-element terminal to three respective coils included in a first X-ray tube that is driven by three-phase alternating current power.

5. The X-ray diagnosis system according to claim 1, wherein a single-phase half bridge inverter circuit is formed by connecting the inter-capacitor terminal to a common terminal of a second X-ray tube that is driven by two-phase alternating current power, and by connecting two of the first inter-switching-element terminal, the second inter-switching-element terminal, and the third inter-switching-element terminal to two respective coils included in the second X-ray tube.

6. The X-ray diagnosis system according to claim 2, wherein a single-phase half bridge inverter circuit is formed by connecting the inter-capacitor terminal to a common terminal of a second X-ray tube, and by connecting two of the first inter-switching-element terminal, the second inter-switching-element terminal, and the third inter-switching-element terminal to two respective coils included in the second X-ray tube driven by two-phase alternating current power.

7. The X-ray diagnosis system according to claim 3, wherein a single-phase half bridge inverter circuit is formed by connecting the inter-capacitor terminal to a common terminal of a second X-ray tube, and by connecting two of the first inter-switching-element terminal, the second inter-switching-element terminal, and the third inter-switching-element terminal to two respective coils included in the second X-ray tube driven by two-phase alternating current power.

8. The X-ray diagnosis system according to claim 1, further comprising switching element driving circuitry configured to control ON and OFF of each of the switching elements in such a manner that a three-phase alternating current is supplied to a first X-ray tube that is driven by three-phase alternating current power, and to control ON and OFF of the switching elements to generate a two-phase alternating current for a second X-ray tube that is driven by two-phase alternating current power.

9. The X-ray diagnosis system according to claim 2, further comprising switching element driving circuitry configured to control ON and OFF of each of the switching elements in such a manner that a three-phase alternating current is supplied to a first X-ray tube that is driven by three-phase alternating current power, and to control ON and OFF of the switching elements to generate a two-phase alternating current for a second X-ray tube that is driven by two-phase alternating current power.

10. The X-ray diagnosis system according to claim 3, further comprising switching element driving circuitry configured to control ON and OFF of each of the switching elements in such a manner that a three-phase alternating current is supplied to a first X-ray tube that is driven by three-phase alternating current power, and to control ON and OFF of the switching elements to generate a two-phase alternating current for a second X-ray tube that is driven by two-phase alternating current power.

11. The X-ray diagnosis system according to claim 7, further comprising switching element driving circuitry configured to control ON and OFF of each of the switching elements in such a manner that a three-phase alternating current is supplied to a first X-ray tube that is driven by three-phase alternating current power, and to control ON and OFF of the switching elements to generate a two-phase alternating current for a second X-ray tube that is driven by two-phase alternating current power.

12. The X-ray diagnosis system according to claim 7, wherein
the first X-ray tube and the second X-ray tube are driven by a predetermined voltage,
an input voltage to the three-phase full-bridge inverter circuit is the predetermined voltage, and
an input voltage to the single-phase half bridge inverter circuit is a voltage twice the predetermined voltage.

13. The X-ray diagnosis system according to claim 11, wherein
the first X-ray tube and the second X-ray tube are driven by a predetermined voltage,
an input voltage to the three-phase full-bridge inverter circuit is the predetermined voltage, and
an input voltage to the single-phase half bridge inverter circuit is a voltage twice the predetermined voltage.

14. The X-ray diagnosis system according to claim 1, further comprising:
AC/DC converter circuitry configured to generate a direct-current voltage from an alternating current supplied from a power source;
a step-up/step-down converter that is inserted between the AC/DC converter circuitry and the two capacitors, and configured to apply a voltage resultant of stepping up or stepping down the direct-current voltage to the two capacitors; and
step-up/step-down switching circuitry configured to switch to a configuration in which the step-up/step-down converter steps up the direct-current voltage, a configuration in which the step-up/step-down converter steps down the direct-current voltage, and to a configuration in which the step-up/step-down converter does neither step up nor step down the direct-current voltage.

15. The X-ray diagnosis system according to claim 2, further comprising:
AC/DC converter circuitry configured to generate a direct-current voltage from an alternating current supplied from a power source;
a step-up/step-down converter that is inserted between the AC/DC converter circuitry and the two capacitors, and configured to apply a voltage resultant of stepping up or stepping down the direct-current voltage to the two capacitors; and
step-up/step-down switching circuitry configured to switch to a configuration in which the step-up/step-down converter steps up the direct-current voltage, to a configuration in which the step-up/step-down converter steps down the direct-current voltage, and to a configuration in which the step-up/step-down converter does neither step up nor step down the direct-current voltage.

16. The X-ray diagnosis system according to claim 14, wherein
the step-up/step-down converter comprises:
a step-up/step-down coil;
a first step-up/step-down switching element and a second step-up/step-down switching element that are serially connected to one end of the step-up/step-down coil interposed therebetween; and
step-up/step-down switching element driving circuitry configured to supply a voltage pulse to the first step-up/step-down switching element and the second step-up/step-down switching element, and
the step-up/step-down switching circuitry is configured:
to connect a low-voltage-side terminal of the step-up/step-down converter to a low-voltage-side terminal of the AC/DC converter circuitry and to a low-voltage-side terminal of the two capacitors, when the direct-current voltage is to be stepped up and when the direct-current voltage is stepped down,
to connect a high-voltage-side terminal of the step-up/step-down converter to a high-voltage-side terminal of the two capacitors, and to connect another end of the step-up/step-down coil to a high-voltage-side terminal of the AC/DC converter circuitry when the direct-current voltage is to be stepped up,
to connect the high-voltage-side terminal of the step-up/step-down converter to the high-voltage-side terminal of the AC/DC converter circuitry, and to connect the other end of the step-up/step-down coil to the high-voltage-side terminal of the two capacitors when the direct-current voltage is stepped down, and
to connect the high-voltage-side terminal of the AC/DC converter circuitry to the high-voltage-side terminal of the two capacitors, and to connect the low-voltage-side terminal of the AC/DC converter circuitry to the low-voltage-side terminal of the two capacitors when the direct-current voltage is neither stepped down nor stepped down.

17. The X-ray diagnosis system according to claim 1, further comprising:
   AC/DC converter circuitry configured to generate a direct-current voltage from an alternating current supplied from a power source;
   a step-up converter that is inserted between the AC/DC converter circuitry and the two capacitors, and configured to apply a voltage resultant of stepping up the direct-current voltage to the two capacitors; and
   step-up switching circuitry configured to switch to a configuration in which the step-up converter steps up the direct-current voltage, and to a configuration in which the step-up converter does not step up the direct-current voltage.

18. The X-ray diagnosis system according to claim 17, wherein the step-up converter comprises:
   a step-up coil;
   a diode having an anode connected to one end of the step-up coil;
   a step-up switching element having one end connected to the one end of the step-up coil; and
   step-up switching element driving circuitry configured to supply a voltage pulse to the step-up switching element, and
   the step-up switching circuitry is configured:
   to connect a cathode of the diode to a high-voltage-side terminal of the two capacitors, to connect another end of the step-up switching element to a low-voltage-side terminal of the AC/DC converter circuitry and to a low-voltage-side terminal of the two capacitors, and to connect another end of the step-up coil to a high-voltage-side terminal of the AC/DC converter circuitry, when the direct-current voltage is to be stepped up, and
   to connect the high-voltage-side terminal of the AC/DC converter circuitry to the high-voltage-side terminal of the two capacitors, and to connect the low-voltage-side terminal of the AC/DC converter circuitry to the low-voltage-side terminal of the two capacitors, when the direct-current voltage is not to be stepped up.

19. The X-ray diagnosis system according to claim 18, further comprising switching element driving circuitry configured to control inverter circuitry implemented as switching circuitry configured to switch to a connection to the first inter-switching-element terminal, the second inter-switching-element terminal, and the third inter-switching-element terminal, and a connection to the inter-capacitor terminal and the two of the first inter-switching-element terminal, the second inter-switching-element terminal, and the third inter-switching-element terminal, wherein
   the switching element driving circuitry is configured to shorten time for which each of the switching elements included in the inverter circuitry is ON, or to modulate an ON signal for switching each of the switching elements included in the inverter circuitry to ON, when a voltage resultant of stepping down the direct-current voltage is to be supplied to the two capacitors.

20. An anode-rotating coil driver comprising:
   an inter-capacitor terminal that is provided between two capacitors that are serially connected to each other;
   a first inter-switching-element terminal that is provided between two first switching elements that are serially connected to each other;
   a second inter-switching-element terminal that is provided between two second switching elements that are serially connected to each other; and
   a third inter-switching-element terminal that is provided between two third switching elements that are serially connected to each other, wherein
   the first inter-switching-element terminal, the second inter-switching-element terminal, and the third inter-switching-element terminal are configured to supply three-phase alternating current power, and the inter-capacitor terminal and two of the first inter-switching-element terminal, the second inter-switching-element terminal, and the third inter-switching-element terminal are configured to supply two-phase alternating current power.

* * * * *